(12) United States Patent
Servidio et al.

(10) Patent No.: US 11,857,426 B2
(45) Date of Patent: Jan. 2, 2024

(54) FIXATION DEVICES AND PROSTHESES FOR SOFT TISSUE CONNECTION TO THE SAME

(71) Applicant: Howmedica Osteonics Corp., Mahwah, NJ (US)

(72) Inventors: Damon J. Servidio, Towaco, NJ (US); G. Douglas Letson, Tampa, FL (US); Arlen Dale Hanssen, Rochester, MN (US); Michael A. McGovern, Ramsey, NJ (US); Jennifer Grunden, Naples, FL (US)

(73) Assignee: Howmedica Osteonics Corp., Mahwah, NJ (US)

( * ) Notice: Subject to any disclaimer, the term of this patent is extended or adjusted under 35 U.S.C. 154(b) by 91 days.

(21) Appl. No.: 17/545,020

(22) Filed: Dec. 8, 2021

(65) Prior Publication Data
US 2022/0087826 A1 Mar. 24, 2022

Related U.S. Application Data

(63) Continuation of application No. 16/524,534, filed on Jul. 29, 2019, now Pat. No. 11,219,528.
(Continued)

(51) Int. Cl.
*A61F 2/38* (2006.01)
*A61F 2/30* (2006.01)
(Continued)

(52) U.S. Cl.
CPC .......... *A61F 2/389* (2013.01); *A61F 2/30771* (2013.01); *A61F 2/30907* (2013.01);
(Continued)

(58) Field of Classification Search
CPC .... A61F 2/389; A61F 2/0811; A61F 2/30771; A61F 2002/30604; A61F 2/367
See application file for complete search history.

(56) References Cited

U.S. PATENT DOCUMENTS

| 1,064,724 A | 6/1913 | Guett |
| 5,013,324 A | 5/1991 | Zolman et al. |
| (Continued) | | |

FOREIGN PATENT DOCUMENTS

| EP | 3046294 A1 | 7/2016 |
| WO | 9103993 A1 | 4/1991 |

OTHER PUBLICATIONS

Extended European Search Report for Application No. EP 19188800.7 dated Oct. 24, 2019, 8 pages.

*Primary Examiner* — Javier G Blanco
(74) *Attorney, Agent, or Firm* — Lerner David LLP

(57) ABSTRACT

An orthopedic assembly includes a tibial prosthesis that includes a body that defines an anterior side and a posterior side. The body further incudes a recess in the anterior side of the joint prosthesis and a plurality of openings that extend through the body from the anterior side to the posterior side thereof. At least a first and second opening of the openings are positioned at respective lateral and medial sides of a longitudinal axis of the tibial prosthesis. A modular insert is positioned within the recess of the body such that at least a portion of the modular insert is positioned between the openings of the body. The modular insert is formed separately from the tibial prosthesis and has a porous outer surface to promote tissue ingrowth.

19 Claims, 25 Drawing Sheets

Related U.S. Application Data

(60) Provisional application No. 62/791,461, filed on Jan. 11, 2019, provisional application No. 62/712,491, filed on Jul. 31, 2018.

(51) Int. Cl.
*A61F 2/08* (2006.01)
*A61F 2/36* (2006.01)

(52) U.S. Cl.
CPC ............. *A61F 2/0811* (2013.01); *A61F 2/367* (2013.01); *A61F 2002/3092* (2013.01); *A61F 2002/3093* (2013.01); *A61F 2002/30385* (2013.01); *A61F 2002/30405* (2013.01); *A61F 2002/30461* (2013.01); *A61F 2002/30604* (2013.01); *A61F 2002/30914* (2013.01)

(56) References Cited

U.S. PATENT DOCUMENTS

| | | |
|---|---|---|
| 6,592,622 B1 | 7/2003 | Ferguson |
| 7,001,429 B2 | 2/2006 | Ferguson |
| 7,070,622 B1 | 7/2006 | Brown et al. |
| 8,177,849 B2 | 5/2012 | Meyers et al. |
| 8,182,542 B2 | 5/2012 | Ferko |
| 8,226,725 B2 | 7/2012 | Ferko |
| 8,292,967 B2 | 10/2012 | Brown et al. |
| 8,636,800 B2 | 1/2014 | Ferko et al. |
| 8,715,356 B2 | 5/2014 | Porter et al. |
| 8,979,940 B2 | 3/2015 | Porter et al. |
| 9,005,305 B2 | 4/2015 | Meyers et al. |
| 9,833,326 B2 | 12/2017 | Porter et al. |
| 10,251,744 B2 | 4/2019 | Treacy et al. |
| 10,463,685 B2 | 11/2019 | Shay et al. |
| 2003/0216809 A1 | 11/2003 | Ferguson |
| 2011/0009973 A1 | 1/2011 | Meyers et al. |
| 2011/0213467 A1 | 9/2011 | Lozier et al. |
| 2013/0226204 A1 | 8/2013 | Kumar |
| 2014/0025166 A1 | 1/2014 | Bonutti |
| 2014/0207242 A1 | 7/2014 | Vrahas |
| 2018/0214261 A1 | 8/2018 | Treacy et al. |

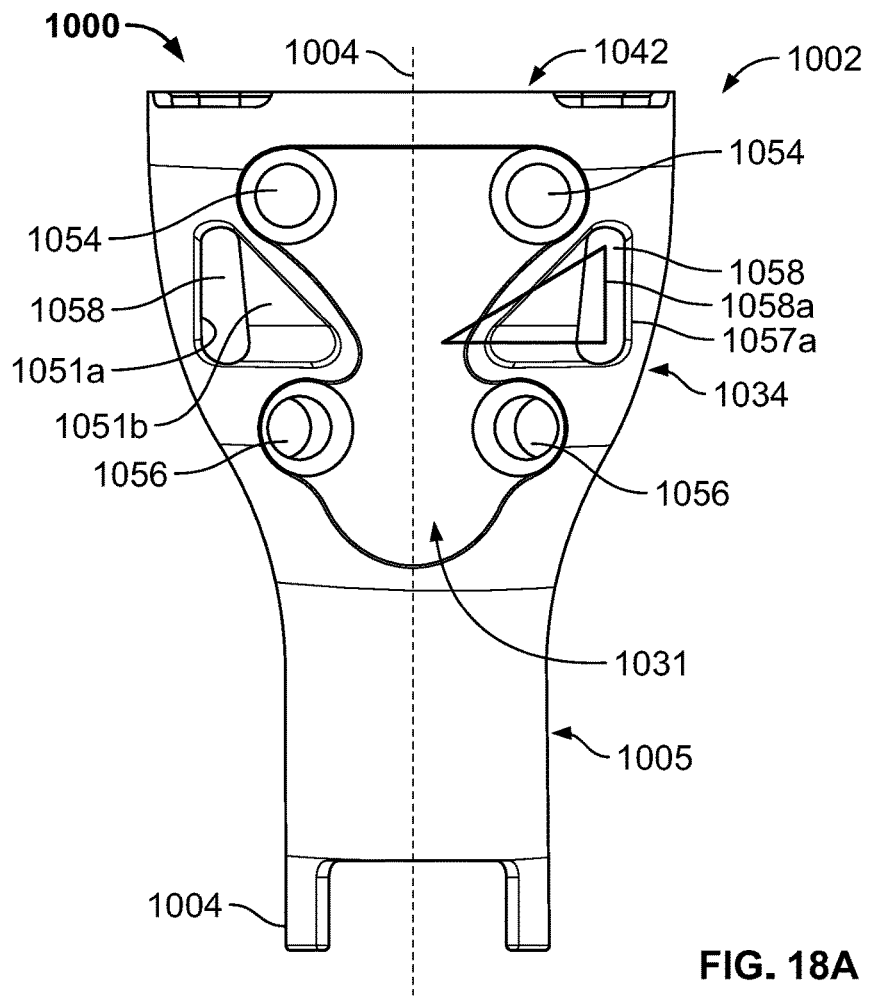
FIG. 18A
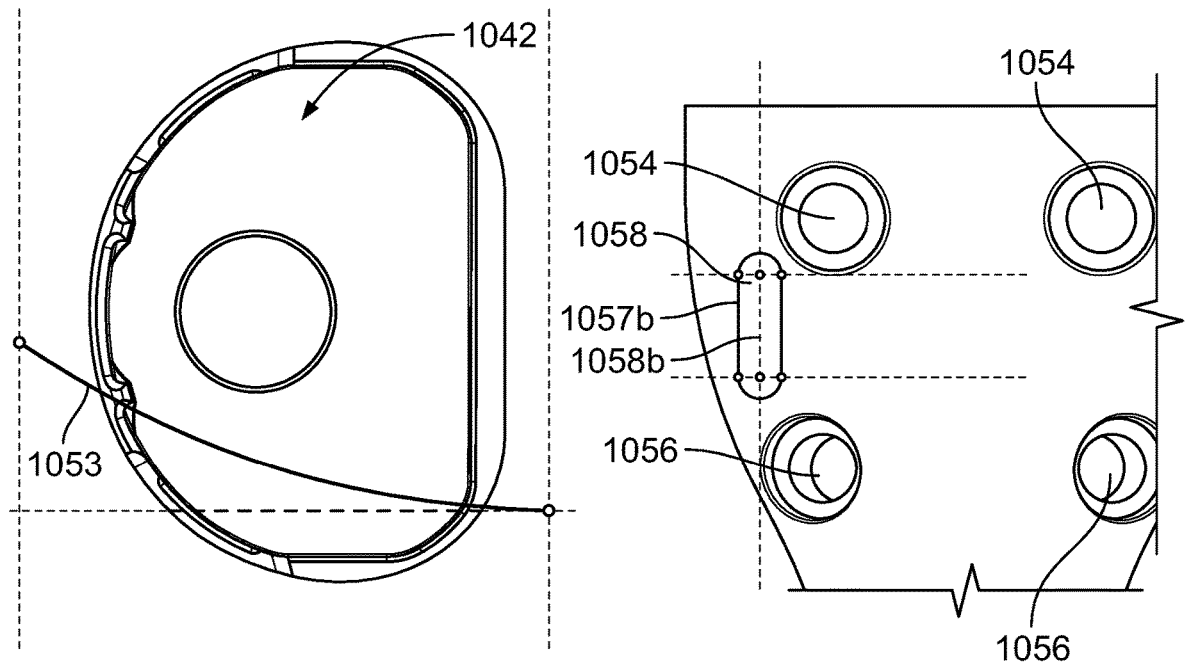
FIG. 18B  FIG. 18C

FIXATION DEVICES AND PROSTHESES FOR SOFT TISSUE CONNECTION TO THE SAME

CROSS-REFERENCE TO RELATED APPLICATIONS

This application is a continuation of U.S. application Ser. No. 16/524,534, filed on Jul. 29, 2019, which claims the benefit of the filing date of U.S. Provisional Application No. 62/712,491, filed on Jul. 31, 2018, and U.S. Provisional Application No. 62/791,461, filed on Jan. 11, 2019, the disclosures of which are hereby incorporated by reference in their entireties.

BACKGROUND OF THE INVENTION

Joint replacement surgery is an orthopedic procedure in which a surface of a diseased or a damaged joint is replaced with an orthopedic prosthesis designed to replicate the movement of a normal, healthy joint. In such orthopedic procedure, a patient's joint is typically replaced with prosthetic components by resecting a portion of the patient's bone and/or cartilage to create a platform, a recess, or a cavity for receiving a portion of the prosthetic components being implanted. Thereafter, the prosthetic components are affixed to the resected bone. However, in addition to replacing the joint surfaces of the prosthesis, some joint replacement surgeries may also require attachment of soft tissue to an underlying support structure, such as bone or the joint prosthesis itself.

In one example, a revision joint replacement surgery typically involves the replacement of a primary prosthesis or a previously implanted revision prosthesis. Such surgery may additionally involve the correction of complications resulting from a joint replacement surgery. Such complications include suprapatellar, transpatellar, or infrapatellar extensor mechanism disruption which may occur either intra-operatively (e.g., as a result of improper patellar resection, damage to the blood supply due to injudicious lateral retinacular release, and the like) or in the immediate post-operative period (e.g., as a result of tissue necrosis arising from infection, component malalignment, and the like) of a total knee arthroplasty. Though non-surgical means may address the extensor mechanism disruption, based on the complexity and extent of the disruption, surgical intervention may be necessary.

In another example, a significant amount of bone may be removed from an end of a patient's long bone. This may be due to a cancerous tumor, such as in the distal femur or proximal tibia, or perhaps due to severe trauma. In such a procedure, the connection points between soft tissue and bone are often removed along with the resected bone. For example, a tibial tubercle, which is the connection point for a patellar tendon, may be removed in one of these procedures. In this regard, the tendon is left with no natural connecting structures.

In the above circumstances, along with others not mentioned, attachment of soft tissue (e.g., ligaments and tendons) necessary for functional operation of the corresponding joint may be difficult particularly where long term fixation of the tissue is required. In response to this difficulty, certain devices have been devised. For example, current prostheses that address soft tissue connection typically have openings in their solid structure which allows soft tissue to be sutured thereto by threading wiring, such as cerclage wire, or suture through the soft tissue and through the openings available on the prosthesis. However, such a configuration requires the suture or wires to maintain the connection of the soft tissue to the prosthesis over extended periods of time all the while forces are imposed on the soft tissue via normal joint movements. In this regard, if a single suture or wire fails, the connection between soft tissue and joint prosthesis may be compromised. Thus, further improvements are desirable.

BRIEF SUMMARY OF THE INVENTION

Generally, disclosed herein are orthopedic assemblies and methods for attaching soft tissue to such orthopedic assemblies. In particular, such assemblies are each described as including a joint prosthesis and a filamentary attachment structure which connects to the joint prosthesis. The filamentary attachment structure allows soft tissue to be connected thereto and facilitates tissue ingrowth therein to facilitate a strong long-term connection.

In one aspect of the present disclosure, an orthopedic assembly includes a tibial component having a baseplate, a stem, and a keel. The baseplate includes an upper articulating surface and lower surface disposed opposite the upper articulating surface. The stem and the keel extend from the lower surface, and the keel is positioned adjacent to the stem. The orthopedic assembly also includes a filamentary receiving component that includes a first portion and a second portion. The first portion includes an upper surface corresponding to the lower surface of the baseplate and an opening extending through the first portion which is configured to receive the stem and the keel therein. The second portion extends from an anterior end of the first portion.

Additionally, when the stem is inserted into an intramedullary canal of a proximal tibia, the first portion of the filamentary receiving component may be positioned between the lower surface of the baseplate and the proximal tibia such that the first portion of the filamentary receiving component may be sandwiched therebetween. The upper articulating surface is configured to articulate with a femoral articulating surface, and the femoral articulating surface includes a lateral femoral condyle and a medial femoral condyle on a distal end of a femur. An anterior surface of the second portion of the filamentary receiving component may be configured to connect to soft tissue and includes a portion thereof that tapers away from the first portion. The second portion of the filamentary receiving component may include a filamentary material configured for securing soft tissue thereto. The filamentary material may be selected from the group consisting of: a synthetic polymer, a bioresorbable fiber, a ceramic/a glass, a biological material, a pharmacological agent, and combinations thereof.

Continuing with this aspect, a thickness between the upper surface of the first portion and a lower surface of the first portion may be smaller than a distance from a perimeter of the first portion and the opening of the first portion. The opening may extend along a central axis. The central axis may extend perpendicular to the upper surface of the first portion of the filamentary receiving component. The keel may comprise at least two fins extending radially outward from the stem towards a posterior end of the baseplate. The opening may be defined by a central cylindrical portion and a lobe portion extending outwardly from the central cylindrical portion. The central cylindrical portion may be configured to receive the stem and the lobe portion may be configured to receive the keel. The lower surface of the baseplate and the upper surface of the filamentary receiving component may be planar.

In another aspect of the present disclosure, a method for attaching soft tissue to a joint replacement assembly includes a joint replacement prosthesis and a receiving component includes inserting a stem of the joint replacement prosthesis into the receiving component. The receiving component includes a first portion and a second portion extending from the first portion, and the joint replacement prosthesis includes an articular portion and a bone abutment portion disposed opposite the articular portion. The stem extends from the bone abutment portion. The method also includes inserting the stem of the joint replacement prosthesis into a bone so that the first portion of the receiving component is positioned between the bone abutment portion and the bone, and so that the second portion extends towards the articular portion of the joint replacement prosthesis. The method further includes securing soft tissue to the second portion of the receiving component.

Additionally, the method may include, prior to inserting the stem of the joint replacement prosthesis into the receiving component, applying an adhesive substance to the bone abutment portion of the joint replacement prosthesis. The adhesive substance may be a bone cement. The second portion of the receiving component may include a filamentary material, and the filamentary material may be selected from the group consisting of: a synthetic polymer, a bioresorbable fiber, a ceramic/a glass, a biological material, a pharmacological agent, and combinations thereof. Also, the step of securing the soft tissue to the second portion of the receiving component may include suturing the soft tissue to the second portion. The second portion of the receiving component may include one or more suture holes. The second portion of the receiving component may be made from a knitted or woven filamentary material and the one or more suture holes may be defined by the knitted or woven filamentary material. Also, the step of securing the soft tissue to the second portion of the receiving component may include threading cerclage wire through the one or more suture holes of the second portion and through the soft tissue. The method may further include threading the cerclage wire through openings in the joint replacement prosthesis.

Continuing with this aspect, the method may further include securing the soft tissue directly to the joint replacement assembly via a threaded connection or a wired connection. The bone may be a tibia, and the soft tissue may be a patellar tendon.

In a further aspect of the present disclosure, an orthopedic assembly includes a tibial component that includes a baseplate, a stem, and a keel. The baseplate includes an upper articulating surface and a planar lower surface disposed opposite the upper articulating surface. The stem and the keel extending from the planar lower surface, and the keel includes a first fin positioned adjacent to the stem. The assembly also includes a filamentary receiving component that includes a first portion and a second portion. The first portion includes an upper surface, a lower surface, and an opening extending through the upper and lower surfaces. The opening includes a main region and a first offset region in communication with the main region. The main region is configured to receive the stem, and the first offset region is configured to receive the first fin.

Additionally, the second portion may include an attachment region located on an anterior surface of the second portion. The attachment region may include a filamentary material configured to secure a soft tissue thereto. The attachment region may further include one or more porous surfaces configured to facilitate ingrowth of a bone and/or the soft tissue. The filamentary receiving component may also include a second offset region in communication with the main region. The keel may include a second fin positioned adjacent to the stem, and the second offset region may be configured to receive the second fin. The first offset region may be positioned on a first side of a central axis extending through the main region of the opening, and the second offset region may be positioned on a second side of the central axis. The main region may be cylindrical, and the first and the second offset regions may be elongate and extend away from the main region in both an anteroposterior direction and a mediolateral direction.

In an additional aspect of the present disclosure, an orthopedic assembly includes a tibial prosthesis that includes a body that defines an anterior side and a posterior side. The body further defines a recess in the anterior side of the joint prosthesis and a plurality of openings extending through the body from the anterior side to the posterior side thereof. At least a first and second opening of the openings are positioned at respective lateral and medial sides of a longitudinal axis of the tibial prosthesis. The assembly also includes a modular insert positioned within the recess of the body such that at least a portion of the modular insert is positioned between the openings of the body. The modular insert is formed separately from the tibial prosthesis and has a porous outer surface to promote tissue ingrowth.

Additionally, the modular insert may include a ring portion positioned about a stem of the body and a connection portion extending from the ring portion and positioned within the recess of the body. The connection portion may include at least one protrusion extending therefrom and into a complementary receiving structure of the body. The complementary receiving structure may be located within the recess of the body. The at least one protrusion may be tapered and the complementary receiving structure may be tapered so as to form a taper lock when the protrusion is received in the complementary receiving structure.

Continuing with this aspect, the assembly may also include a filamentary fixation device extending through the first and second openings. The filamentary fixation device may have a first free end and a second free end. The first and second free ends may extend through the respective first and second openings such that the first and second free ends are positioned at the anterior side of the body. The filamentary fixation device may include a filamentary material configured to secure soft tissue thereto. The filamentary material may be selected from the group consisting of a synthetic polymer, a bioresorbable fiber, a ceramic/a glass, a biological material, a pharmacological agent, and combinations thereof. The filamentary fixation device may include a mesh structure for securing soft tissue thereto. The mesh structure may include a plurality of layers. The plurality of layers may be connected by a continuous or interrupted seams. A third opening of the openings in the body may extend in a lateral-medial direction for receipt of a suture therethrough to connect the filamentary fixation device to the body.

Furthermore, the assembly may include cannulated screws. The cannulated screws may connect the modular insert to the body via the first and second holes. The cannulated screws are cannulated such that they each include an opening extending entirely therethrough such that when they are received in the first and second openings of the body, such openings are not entirely occluded by the cannulated screws.

In a further aspect of the present disclosure, an orthopedic assembly includes a joint prosthesis that includes a body. The body has an upper portion and a stem. The upper portion has a recessed portion that has at least one opening extending through the body. The assembly also includes a plate separately formed from the joint prosthesis and has a shape complementary to and received by the recessed portion of the body. The plate has at least one opening extending therethrough and a porous outer surface. The at least one opening of the plate is aligned with the opening of the body when the plate is received by the recessed portion. The assembly further includes a threaded member. The threaded member is cannulated such that an opening extends through the length of the threaded member. The threaded member connects the plate to the joint prosthesis via the openings of the body and plate such that the cannulation of the threaded member prohibits such openings from being completely occluded when the threaded member is received therein.

Additionally, the opening of the threaded member may be configured to receive a suture or a wire. The plate may include an attachment region at an anterior side thereof. The attachment region may include the porous outer surface configured to facilitate the ingrowth of a soft tissue. The porous outer surface may be made from a metallic material. The plate further may further include an indented region at an anterior side thereof for receipt of a segment of bone. The at least one opening of the plate and joint prosthesis may include a first and second opening and one of the threaded member may be disposed in each of the first and second openings of the plate and joint prosthesis to fix the plate to the joint prosthesis.

Continuing with this aspect, the assembly may include a suture or a wire extending through the first and second openings of the plate, joint prosthesis, and respective threaded members thereof. The joint prosthesis may be a tibial prosthesis having a proximal end configured to articulate with a femoral prosthesis. The tibial prosthesis may include a metaphyseal portion and a diaphyseal portion for replacing a respective metaphysis and diaphysis of bone.

In an even further aspect of the present disclosure, an orthopedic system includes a joint prosthesis that has a first portion configured to connect to a resected bone and a second portion configured to interface with a second joint prosthesis. The system also includes a filamentary fixation device for reconstructing soft tissue that has a plurality of layers of a mesh material. Each of the layers is connected to an adjacent layer by at least one seam formed by heat.

Additionally, the plurality of seams may be continuous along the length of the filamentary fixation device. The plurality of seams, alternatively, may be discontinuous along the length of the filamentary fixation device such that the seam extends the full length of the filamentary fixation device but has free segments disposed at regular intervals along the axis of the seam.

In yet further aspect of the present disclosure, an orthopedic assembly includes a tibial prosthesis that includes a body that defines an anterior side and a posterior side. The body further defines first and second slots extending through the posterior and anterior sides of the body. The first and second slots each define a posterior and anterior aperture. The anterior aperture includes a triangular shape. The orthopedic assembly also includes a filamentary fixation device extending through the first and second slots.

Additionally, the posterior aperture may have opposing parallel sides. The posterior aperture may be pill-shaped. Each of the first and second slots may be defined by a first and second sidewall. The first sidewall may tilt away from a central longitudinal axis of the body. The first sidewall may form a hypotenuse of the triangular shaped anterior aperture. The first sidewall may be parallel to the central longitudinal axis at the posterior aperture and may gradually tilt away from the central longitudinal axis along a traversal of the first sidewall from the posterior aperture to the anterior aperture. The first sidewall may decrease in a superior-inferior height along its traversal from the posterior aperture to the anterior aperture. The second sidewall may maintain a constant superior-inferior height along its traversal from the posterior aperture to the anterior aperture. The first sidewall may curve about the central longitudinal axis of the body.

BRIEF DESCRIPTION OF THE FIGURES

A more complete appreciation of the subject matter of the present invention and the various advantages thereof may be realized by reference to the following detailed description, in which reference is made to the following accompanying drawings:

FIG. 18A is a front elevational view of a joint replacement prosthesis according to another embodiment of the present disclosure.

FIG. 18B is a top view of the joint replacement prosthesis of FIG. 18A.

FIG. 18C is a partial rear elevational view of the joint replacement prosthesis of FIG. 18A.

DETAILED DESCRIPTION

Figure 1:
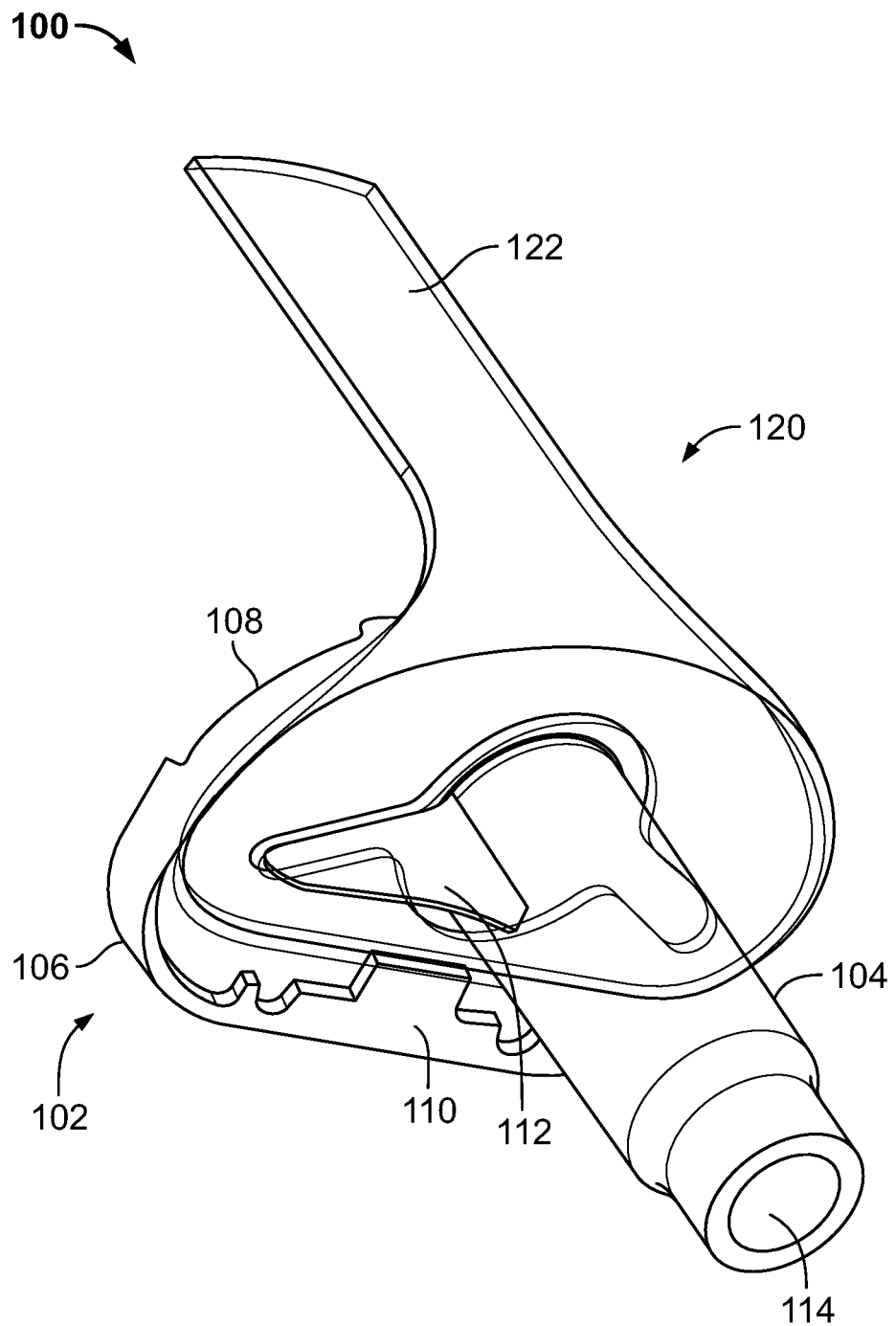
FIG. 1 is a bottom perspective view of a joint replacement assembly according to an embodiment of the present disclosure.

When referring to specific directions in the following discussion of certain implantable joint replacement devices, it should be understood that such directions are described with regard to the orientation and position of the implantable joint replacement devices during exemplary application to the human body. Thus, as used herein, the term "proximal" means situated nearer to the center of the body or the point of attachment and the term "distal" means more situated away from the center of the body or from the point of attachment. The term "anterior" means towards the front part of the body or the face and the term "posterior" means towards the back of the body. The term "medial" means toward the midline of the body and the term "lateral" means away from the midline of the body. Further, as used herein, the terms "about," "generally," and "substantially" are intended to mean deviations from absolute are included within the scope of the term so modified.

FIGS. 1-4 depict a joint replacement assembly 100 comprising a joint replacement prosthesis 102 and a filamentary fixation device 120. The joint replacement prosthesis 102 is a tibial component of a total knee arthroplasty system and is made from biologically suitable material for implantation, such as titanium, stainless steel, cobalt chromium, niobium, and the like. In addition, joint replacement prosthesis 102 may have porous outer surfaces to facilitate bone ingrowth therein.

Joint replacement prosthesis 102 comprises a tibial baseplate 106, a stem boss 104, and a keel 112. Tibial baseplate 106 comprises an insert mating portion 108 and a planar lower surface 110 disposed opposite insert mating portion 108. Planar lower surface 110 is configured to engage a proximal sub-condylar area of a tibia, which is formed by resecting a proximal tibia transverse to an axis thereof. Moreover, planar lower surface 110 may further comprise engagement features (not shown), such as a porous or corrugated surface, or a rim depending downwardly therefrom about a perimeter thereof for engaging the proximal sub-condylar area of the tibia. However, surface 110 is generally understood to be planar.

Stem boss 104 and keel 112 extend from planar lower surface 110. Keel 112, which appears as a wing or blade, is configured to prevent rotation of tibial baseplate 106 and is positioned adjacent stem boss 104. In this regard, keel 112 has a length that extends in a lateral-medial direction, but may also include a component of its travel in an anteroposterior direction. In the particular configuration depicted, prosthesis 102 includes two keels 112a-b, which are integral with baseplate 106 and stem boss 104. However, in some embodiments, only one keel 112 may be provided. Also, keels 112a-b may be modular such that they are not rigidly fixed to either lower surface 110 or stem 104. In still further embodiments, keels 112a-b may be connected to lower surface 110, but not stem boss 104. Regardless, in each of these embodiments, keels 112a-b extends from lower surface 110 and are positioned adjacent stem 104. Stem boss 104 is cylindrical or frustoconical in shape to substantially match a cavity of a bone, such as an intramedullary canal of the tibia. In addition, stem boss 104 is configured to connect to a stem extension (not shown), such as via an opening 114 in stem boss 104.

Figure 2:
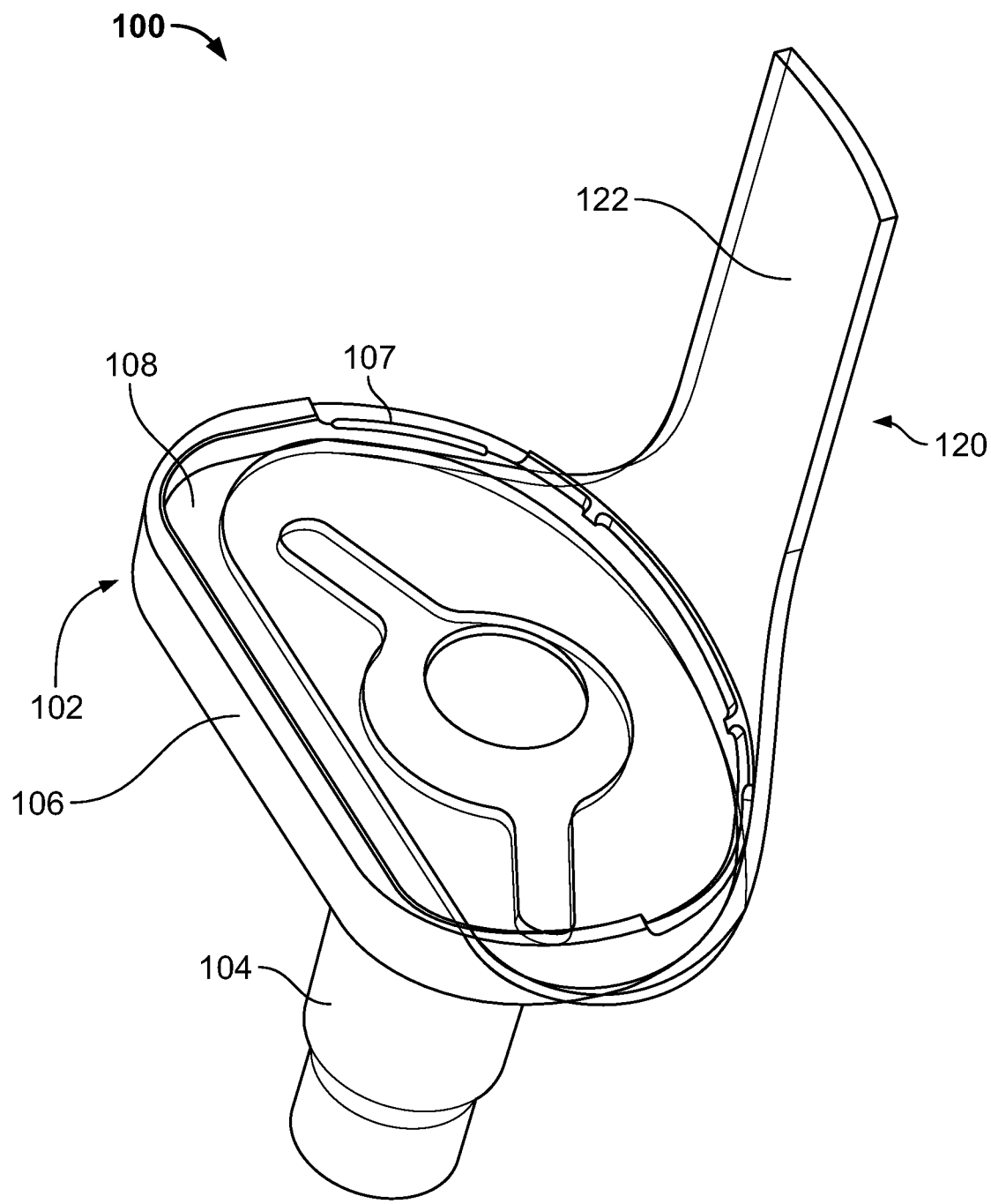
FIG. 2 is a top perspective view of the joint replacement assembly of FIG. 1.

As best shown in FIG. 2, insert mating portion 108 of tibial baseplate 106 is defined by a shoulder portion 107 (e.g., a rim) extending about a periphery of baseplate 106. Such shoulder portion 107 forms a dish or tray configured to receive a tibial bearing component (not shown) where such bearing component includes an articular surface that is configured to articulate with a femoral component, as is understood in the art.

Figure 3:
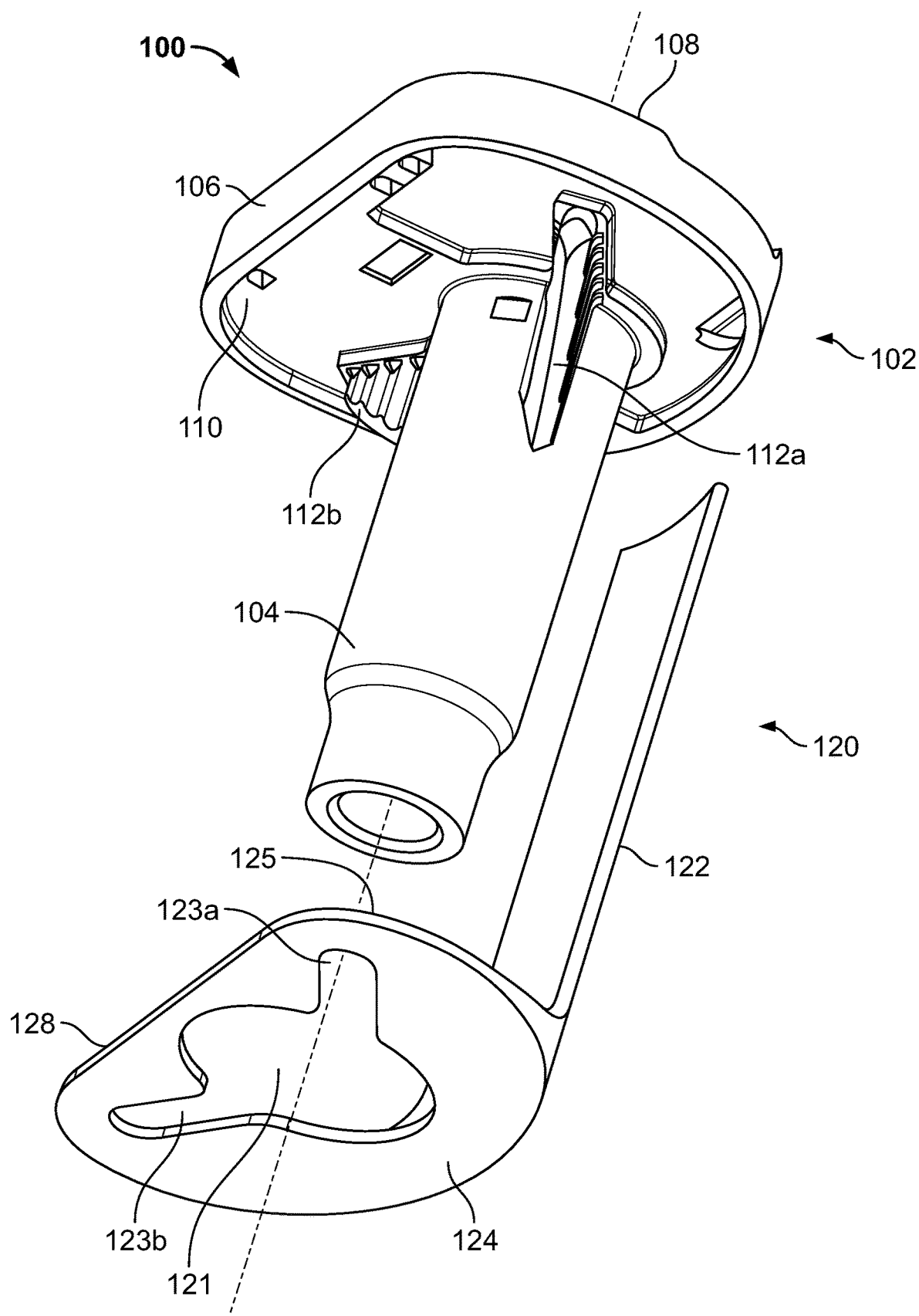
FIG. 3 and FIG. 4 are exploded views of the joint replacement assembly of FIG. 1.
Figure 4:
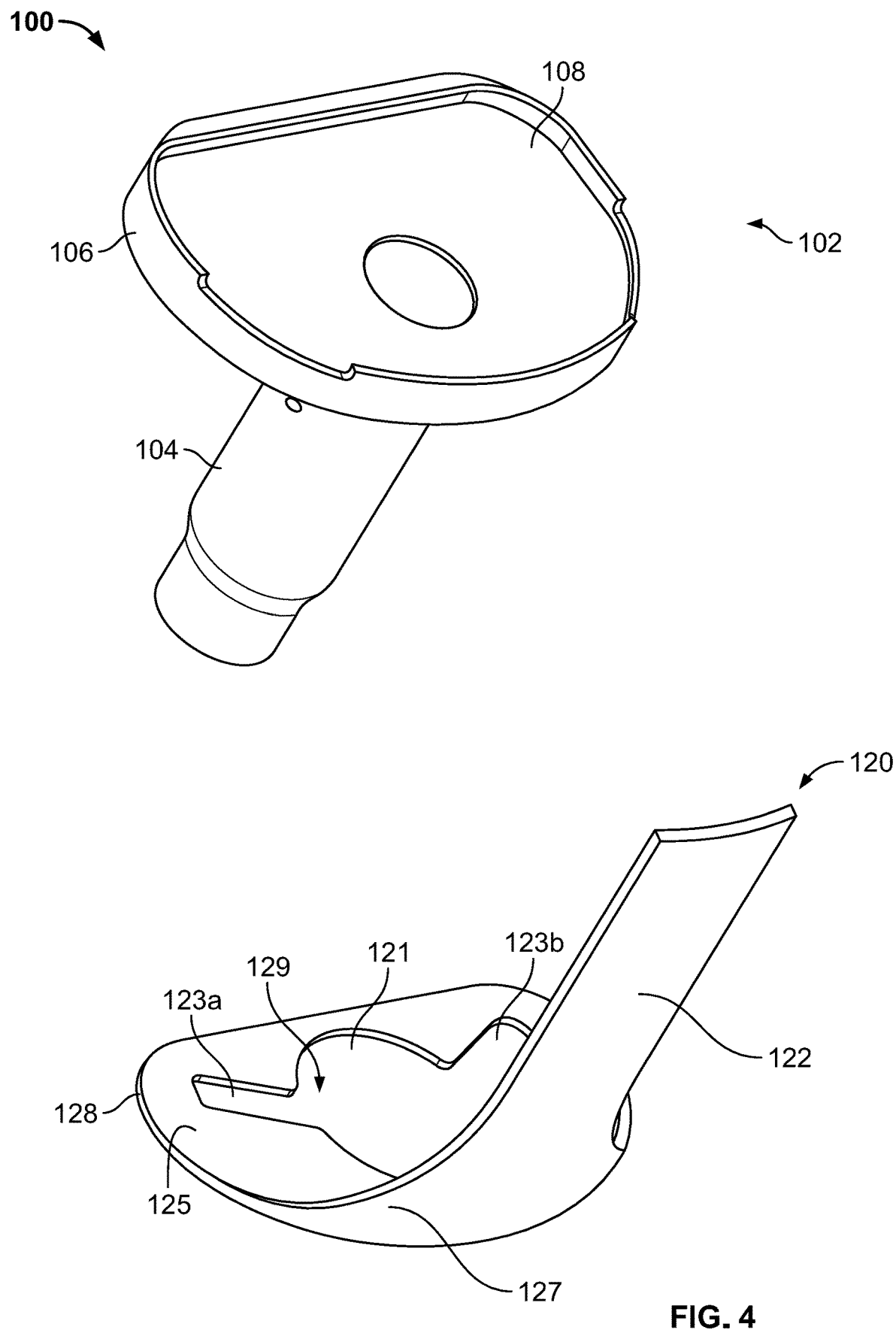

Filamentary receiving component, filamentary fixation device, or filamentary sleeve 120, as best shown in FIGS. 3 and 4, includes a first portion 128 and a second portion 122 extending from an anterior end of first portion 128. First portion 128 has a planar upper surface 125 that corresponds to planar lower surface 110 of tibial baseplate 106. First portion 128 further comprises an opening 129 that extends through first portion 128. A central axis (dotted line in FIG. 3) extends perpendicular to planar upper surface 125 of first portion 128. Opening 129 extends along the central axis and is symmetrical about an anterior-posterior plane in which the central axis lies. A thickness between planar upper surface 125 and a lower surface 124 of first portion 128 is smaller than a distance from a perimeter of first portion 128 and opening 129 of first portion 128.

Opening 129 comprises a main region 121 having a cylindrical shape and lobe portions or offset regions 123a-b extending outwardly from main region 121. Main region 121 is sized and shaped to receive stem boss 104, and lobe portions 123a-b are sized and shaped to receive keels 112.

In this regard, lobe portions 123a-b each extend radially outward from main region 121 both laterally-medially and anteriorly-posteriorly at an angle towards a posterior side of first portion 128 just as keels 112a-b extend from stem boss 104. However, in some embodiments, first lobe 123a and second lobe 123b may extend away from main region 121 in only a mediolateral direction depending on the configuration of keels 112a-b. A shape of first lobe 123a and second lobe 123b is not limited to the depicted and described shape as additional shapes are contemplated. However, the shape of lobes 123a-b generally correspond to a geometry of keels 112a-b so as to conform thereto.

As mentioned above, second portion 122 extends from an anterior side of first portion 128. As shown, second portion 122 also extends in a direction transverse to planar upper surface 125 and away from planar upper surface 125. Also, as shown, second portion 122 has a smaller lateral-medial width than that of first portion 128. In this regard, second portion 122 includes a transition region 127 (see FIG. 4) in which second portion 122 tapers to its more narrow width from first portion 128. Second portion 122 is also generally rectangular in a lateral medial plane and has a larger dimension in a lateral-medial direction than an anteroposterior direction.

Figure 13:
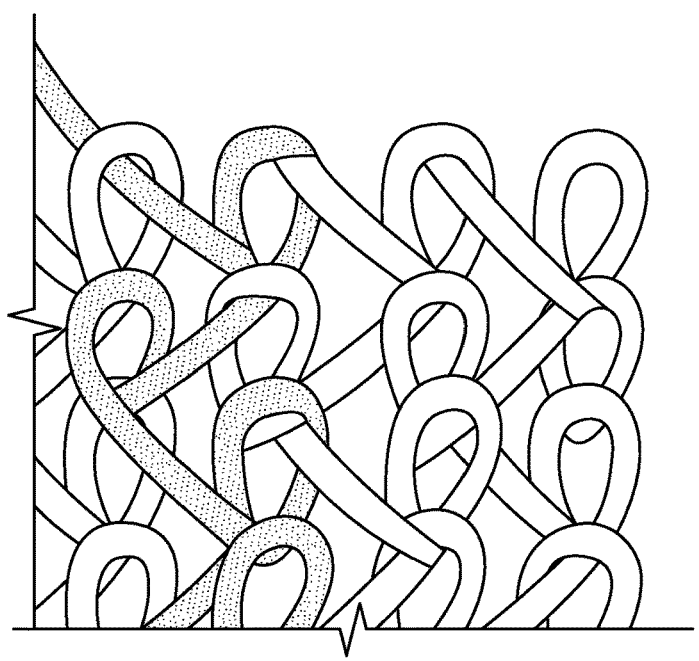
FIG. 13 is a schematic representation of a weave of filamentary material according to an embodiment of the present disclosure.

Filamentary receiving component 120 is made from a filamentary material that may be a knitted or woven material, a non-woven material, or a combination thereof. Such filamentary material may comprise one or more of: a synthetic polymer, a bioresorbable fiber, a ceramic/a glass, a biological material, and a pharmacological agent, among others. The synthetic polymer comprises one or more materials, such as: an ultra-high molecular weight polyethylene (UHMWPE), a polyether-ether-ketone (PEEK), a carbon reinforced PEEK, a polyether-ketone (PEK), a texturized polyethylene terephthalate (PET), an open-weave PET, and a polytetrafluorethylene (PTFE), among others. The bioresorbable fiber comprises one or more materials, such as: a polylacatic acid (PLA), a polyglycolide (PGA), and a poly-L-lactic acid (PLLA), among others. The ceramic/the glass comprises one or more of: an alumina, a zirconia, and a pyrolytic carbon, among others. The biological material comprises one or more materials, such as: a collagen, a silk, and a chitosan, among others. According to some embodiments, the filamentary material of filamentary receiving component 120 comprises a knitted or woven mesh material, such as a monofilament mesh material. It should be appreciated that the listed materials are non-exhaustive and other materials are contemplated herein. However, it should be understood that it is preferable that filamentary receiving component 120 be made from a material that encourages soft tissue growth therein. Thus, a knitted or woven material that has a weave that encourages tissue growth into its porous structure is preferable. An exemplary weave is shown in FIG. 13.

As assembled, filamentary receiving component 120 receives tibial component 102 to form joint replacement prosthesis 100. In this regard, main portion 121 of opening 129 receives stem 104 of tibial baseplate 102, first lobe 123a receives a first keel 112a, and second lobe 123b receives a second keel 112b. Moreover, planar lower surface of baseplate 106 sits generally flush against upper planar surface 125 of first portion 128. The shape of first portion 128 corresponds to the shape of baseplate 106 so that first portion 128 does not extend beyond its perimeter with the exception of near the anterior side thereof where first portion 128 meets second portion 102. In addition, first portion 122 extends upwardly toward mating portion 108 of baseplate 106, as best shown in FIG. 2. First portion 122 extends along the anterior surface of baseplate portion and beyond baseplate 106.

In a method for attaching the soft tissue to the joint replacement prosthesis 102, a previously implanted joint prosthesis may be removed from a proximal tibia. After the proximal tibia is prepared, such as by resecting the proximal tibia, joint replacement assembly 100 is assembled and connected to the tibia. In this regard, filamentary receiving component 120 is engaged to joint prosthesis 102 by inserting stem boss 104 through main portion 121 of opening 129 and keels 122a-b through respective lobe portions 123a-b of opening 129 so that planar lower surface 110 of baseplate 106 is brought into communication with planar upper surface 125 of filamentary receiving component 120. Thereafter, bone cement, such as polymethyl methacrylate (PMMA), is placed on a proximal surface of the tibia and/or on lower surface 124 of first portion 128 of filamentary receiving component 128. In some embodiments, bone cement may even be placed between first portion of filamentary component and baseplate. As shown in FIG. 1, a portion of lower surface 110 of baseplate 106 is not covered by first portion 128. This portion of baseplate 106 also receives bone cement. Once the bone cement is applied, stem boss 104, along with any stem extension attached thereto, is inserted into the intramedullary canal of the tibia and keels 112a-b are driven into the proximal end of the bone until baseplate 106 and filamentary component 120 engage the proximal end of the tibia. Once baseplate 106 is fully seated, first portion 122 of filamentary component 120 is trapped or sandwiched between baseplate 106 and the proximal tibia. Moreover, second portion 122 extends from between the proximal tibia and baseplate 106 and extends superiorly away from the tibia. In this configuration, second portion 122 is well secured by first portion's arrangement between bone and baseplate 106 and also around stem boss 104 and keels 112a-b.

Once assembly 100 is mounted to the tibia, soft tissue is secured to joint replacement prosthesis 102 via filamentary device 120. In this regard, an intact patellar tendon can be attached to filamentary device 120, such as in a revision procedure, to reinforce the tendon from subsequent damage as patellar tendon tears regularly occur postoperatively. Alternatively, a patellar tendon may have been detached from the tibia for any number of reasons. In order to re-secure the intact or detached patellar tendon, the patellar tendon is sewn to a posterior side of second portion 122. Moreover, a muscle, such as the medial gastrocnemius may be sewn to an anterior side of second portion 122 of filamentary component 120 via suture or wire. The arrangement of the patellar tendon and muscle is partially illustrated in FIG. 8. This configuration allows the soft tissue to grow into filamentary component 120 thereby providing a strong long term connection. Thus, filamentary component 120 provides a soft tissue ingrowth structure to prosthesis 102.

Figure 5:
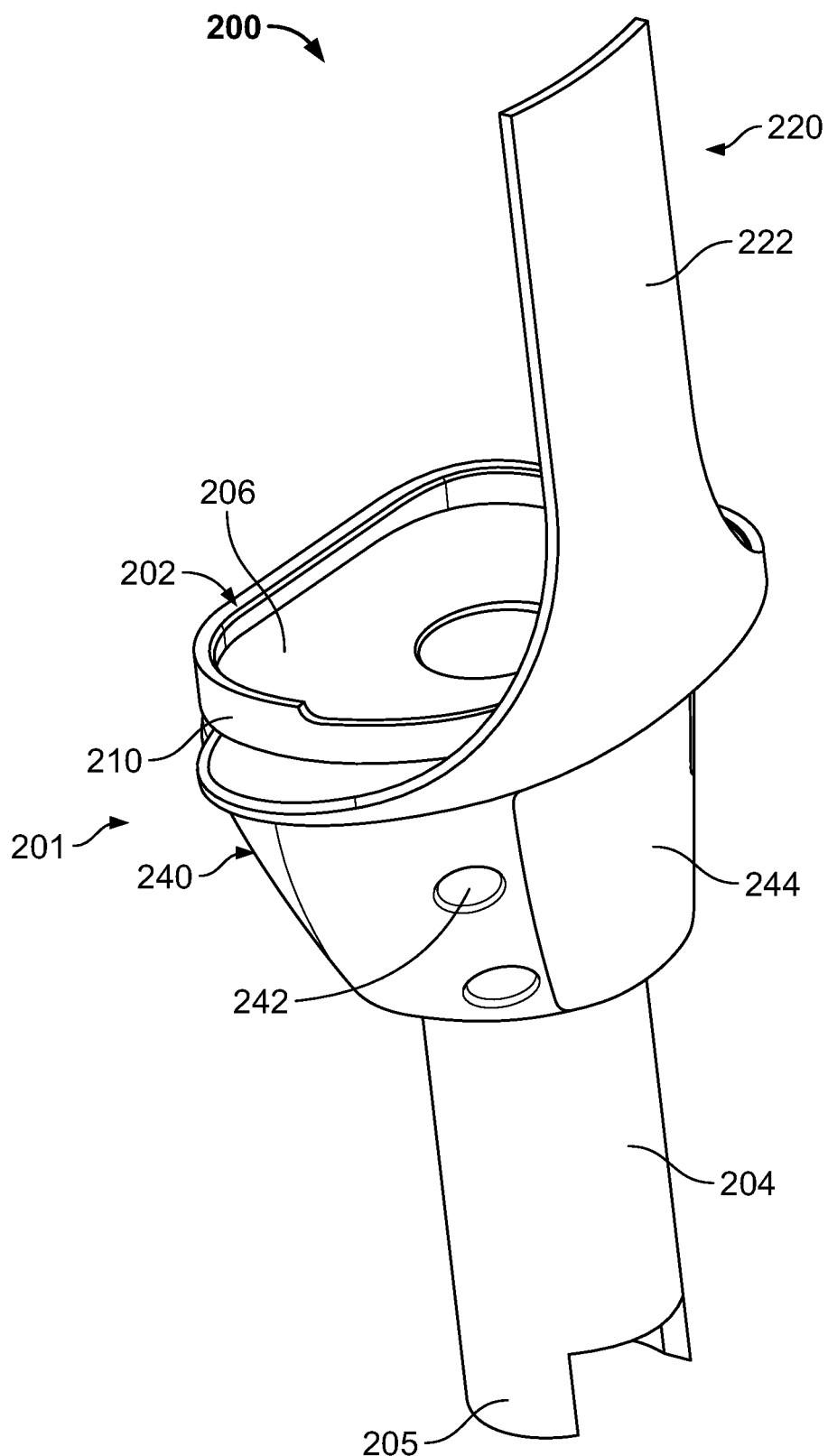
FIG. 5 is a side perspective view of a joint replacement assembly according to another embodiment of the present disclosure.
Figure 6:
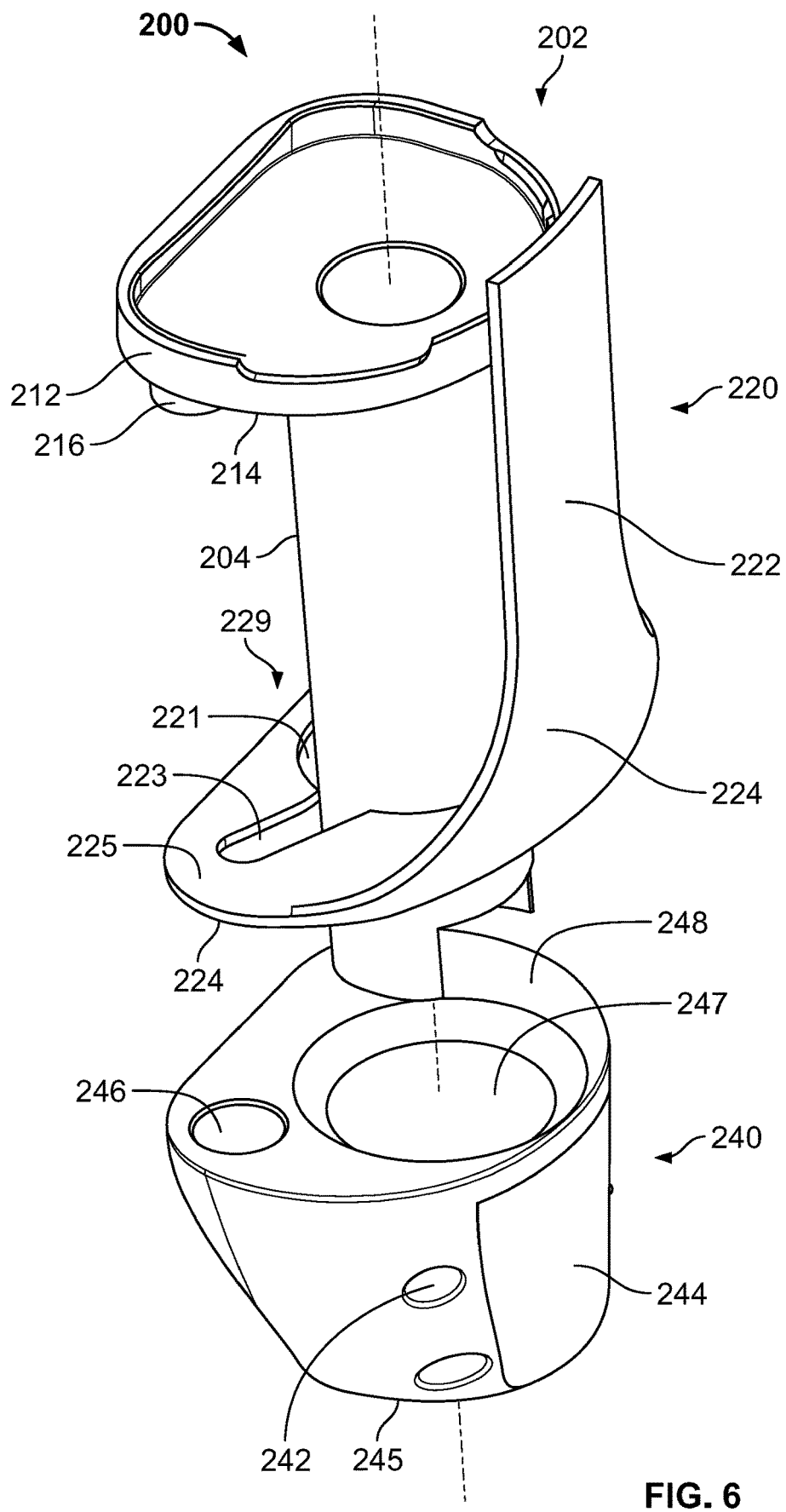
FIG. 6 and FIG. 7 are exploded views of the joint replacement assembly of FIG. 5.
Figure 7:
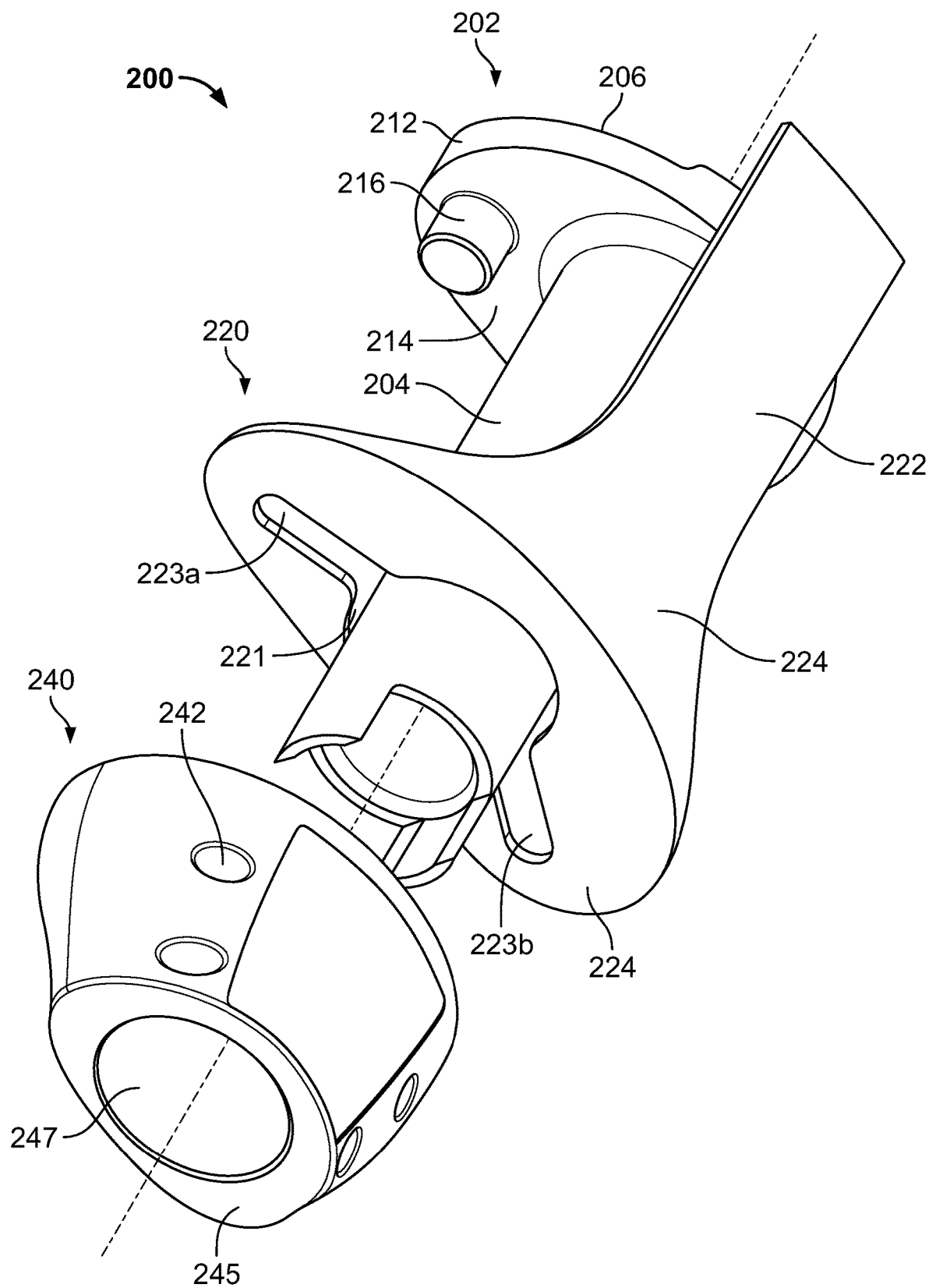

FIGS. 5-7 depict a joint replacement assembly 200 according to another embodiment of the present disclosure. Joint replacement assembly 200 includes joint replacement prosthesis 201 and filamentary receiving component or filamentary fixation device 220.

Joint replacement prosthesis 201 is a tibial prosthesis. However, unlike prosthesis 102 which is a revision tibial prosthesis, prosthesis 201 is configured for use in limb salvage procedures, such as for oncology applications. In this regard, prosthesis 201 comprises a baseplate component 202 that includes a tibial baseplate 212 and a stem 204 extending from tibial baseplate 212. Prosthesis 201 also includes a separately formed body member or metaphyseal member 240 which is connectable to baseplate component 202.

Tibial baseplate 212 comprises an insert mating portion 206 and a planar lower surface 214 disposed opposite insert mating portion 206. Insert mating portion 206 is configured to articulate with a femoral articulating surface on a distal end of a femur. In this regard, insert mating portion 206 may be configured to receive a bearing insert (not shown) similar to baseplate 106, described above. Planar lower surface 214 includes projections or posts 216 extending from a lateral and medial side thereof. Such posts are configured to be received in apertures 246 of body member 240, as discussed below. Stem 204 extends from planar lower surface 214 of tibial baseplate 212 and includes a connection feature 205 at a distal end thereof for connecting to a resected tibial shaft. In this regard, stem 204 acts as a diaphyseal portion of prosthesis 201 for replacing a portion of a diaphysis of a tibia.

Body member 240 is a metaphyseal portion for replacing a metaphysis of a tibia and includes a proximal end, a distal end, and an opening 247 that extends therethrough for receipt of stem 204. The proximal end of body 240 includes a planar surface 248 and apertures 246 extending therein for receipt of posts 216, as best shown in FIG. 6. Such apertures 246 and posts 214 may be correspondingly tapered, such as to form Morse taper locks. An outer surface of body member 240 is tapered so that body 240 expands outwardly in a distal to proximal direction. Additionally, one or more attachment holes 242 and an attachment region 244 are located on the anterior side of body member 240 and are configured for securing a soft tissue to joint replacement assembly 200. In this regard, attachment holes 242 extend in a generally lateral-medial direction through body member 240 so that such attachment holes 242 can receive suture, wire, and the like. Attachment region 244 may also include a patch of filamentary material embedded in the solid structure of body member 244, which can allow soft tissue to be sutured and/or can facilitate tissue growth therein.

Filamentary receiving component 220 is similar to filamentary receiving component 120. In this regard, filamentary receiving component 220 includes a first portion 229 and a second portion 222 extending from first portion 229. First portion 229 includes upper and lower planar surfaces 225, 224 and an opening extending therethrough. The opening includes a main region 221 and adjacent lobe regions 223 similar to those of component 120. However, adjacent lobe regions 223 are configured to receive projections rather than keels 112. Thus, while lobes 223 are shown as communicating with main region 221, such as with component 120, it is contemplated that lobes 223 may not be in communication with main region 221 and, instead, may be positioned remote from main region 221 in respective locations to receive projections 216.

As assembled, stem 204 extends through main region 221 of the opening extending through first portion 229 and through the opening 247 in body member 240, as best illustrated in FIGS. 6 and 7. In addition, projections 216 extend through corresponding lobes 223 and into corresponding apertures 246 in body member 240, which secures body member 240 to baseplate 212. In this configuration, first portion 229 of filamentary receiving component 220 is trapped between planar surface 248 of body member 240 and baseplate 212. This is similar to the finally implanted assembly 100 in which first portion 229 is trapped or sandwiched between baseplate 106 and a proximal tibia. However, in this configuration, first portion 229 is trapped or sandwiched between baseplate 212 and body member 240, rather than between bone and a prosthetic component. In addition, second portion 222 extends from between baseplate 212 and body member 240 and superiorly beyond baseplate 212.

In a method for attaching the soft tissue to joint replacement prosthesis 201, a patellar tendon is detached from the tibial tubercle and a proximal section of the tibia is resected at a location along the tibial shaft so that the removed bone includes the tibial tubercle. Thereafter, filamentary receiving component 220 is engaged to joint prosthesis 201 by inserting stem 204 through opening main region 221 of the opening in first portion 229 and projections 216 extend through lobes 223 into corresponding apertures 246 so that first portion 229 is trapped between surface 248 of body 240 and surface 214 of baseplate 212. Implant 201 is then connected to the bone via connection portion 205.

Once assembly 200 is mounted to the tibia, soft tissue, such as a patellar tendon, is secured to joint replacement assembly by suturing the soft tissue to second portion 222 of filamentary receiving component 220 as described above with respect to assembly 100. The soft tissue may also be secured to joint replacement prosthesis 201 directly by threading wire, such as cerclage wiring, or suture through the soft tissue and through one or more suture holes 242 on joint replacement assembly 200.

Figure 8:
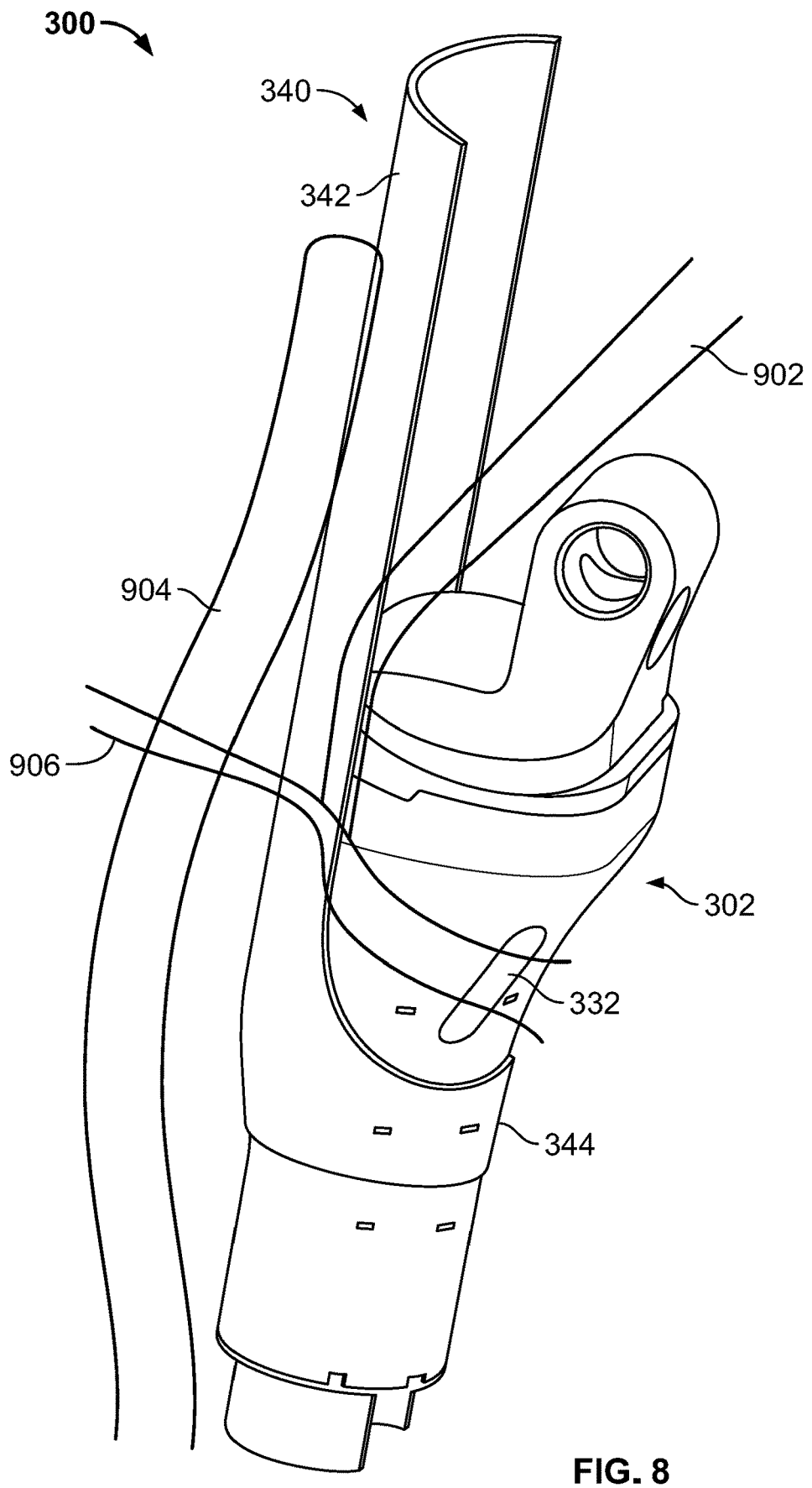
FIG. 8 is a side perspective view of a joint replacement assembly according to a yet further embodiment of the present disclosure including a joint replacement prosthesis and a tissue attachment structure.
Figure 9:
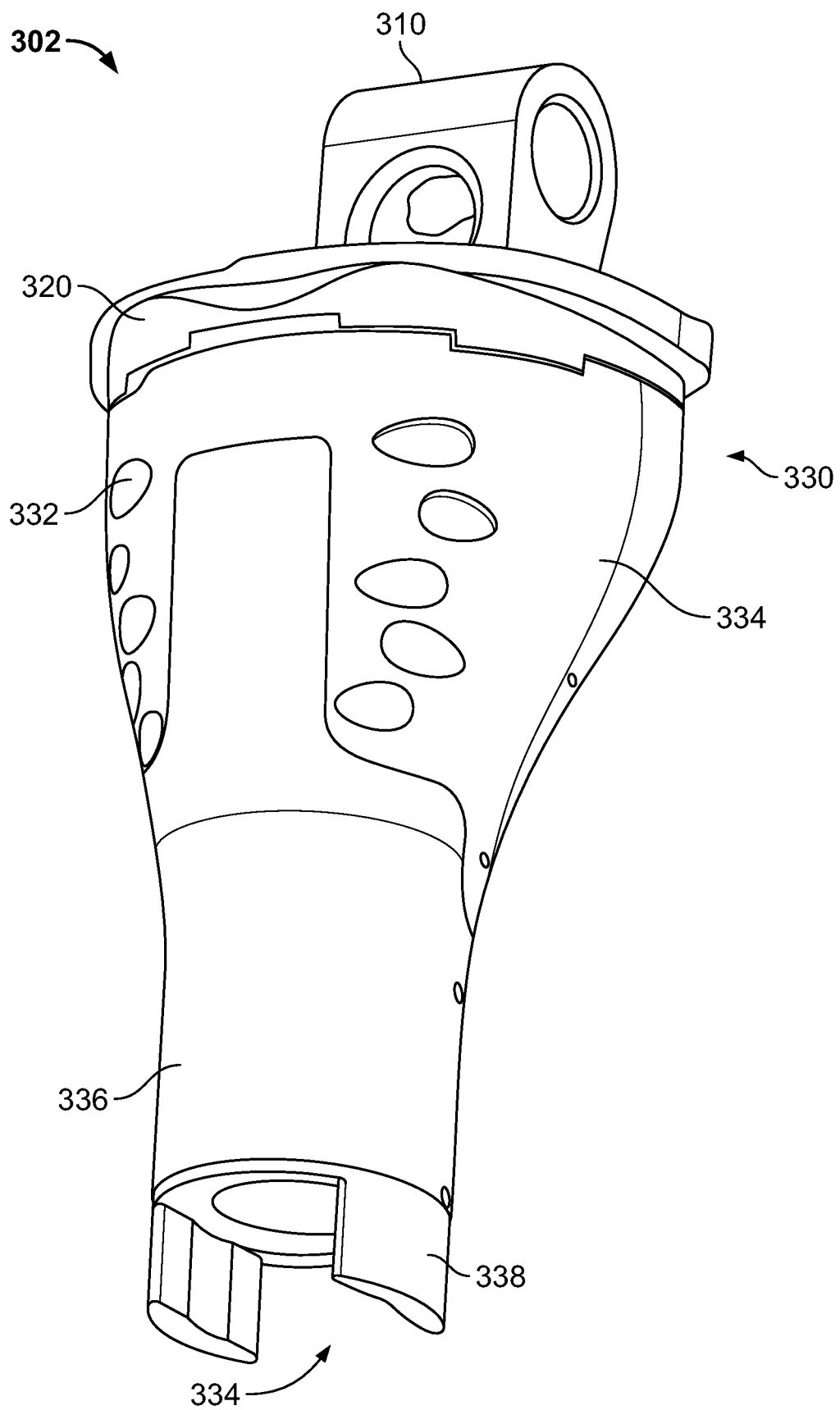
FIG. 9 is a front perspective view of the joint replacement prosthesis of FIG. 8.

FIGS. 8-10B depict a joint replacement assembly 300 according to an even further embodiment of the disclosure. Joint replacement assembly 300, as best shown in FIG. 9, comprises a joint prosthesis 302 and a filamentary receiving component or filamentary fixation device 340. Joint prosthesis 302 is a tibial component of a hinge knee system that may be used in limb salvage procedures, such as for oncology applications. In this regard, prosthesis includes a body 330, a bearing portion 320, and a hinge portion 310 that bears on bearing portion 320. Body 330 has a diaphyseal portion 336 and a metaphyseal portion 334 for replacement of the same of a tibia. At a distal end of diaphyseal portion 336 is a connection feature 338 that allows prosthesis 302 to be connected to a resected portion of a tibial shaft.

Metaphyseal portion 334 includes one or more suture holes or openings 332 located on a medial side and/or a lateral side of an anterior face thereof and extending entirely therethrough. According to some embodiments, a region between suture holes 332 may comprise a material integrated into the structure of body 330 so that body 330 has a patch of filamentary material embedded therein to assist in securing the soft tissue to joint replacement assembly 300 and/or one or more porous surfaces to support tissue ingrowth. Metaphyseal portion 334 is connected to a proximal end of diaphyseal portion 336 so that body 330 tapers outwardly in a distal to proximal direction.

Figure 10A:
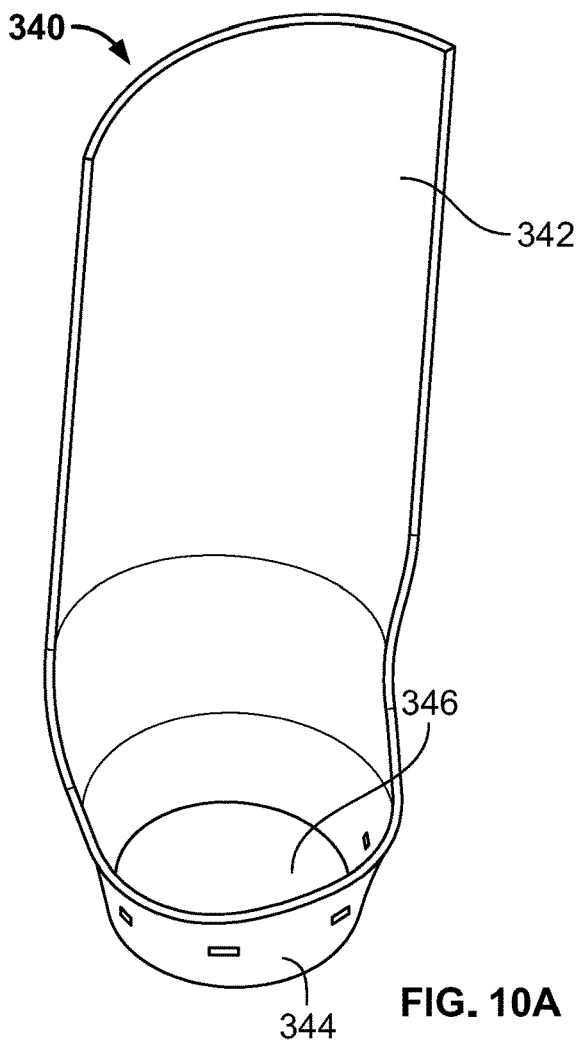
FIG. 10A and FIG. 10B are perspective views of the tissue attachment structure of FIG. 8.
Figure 10B:
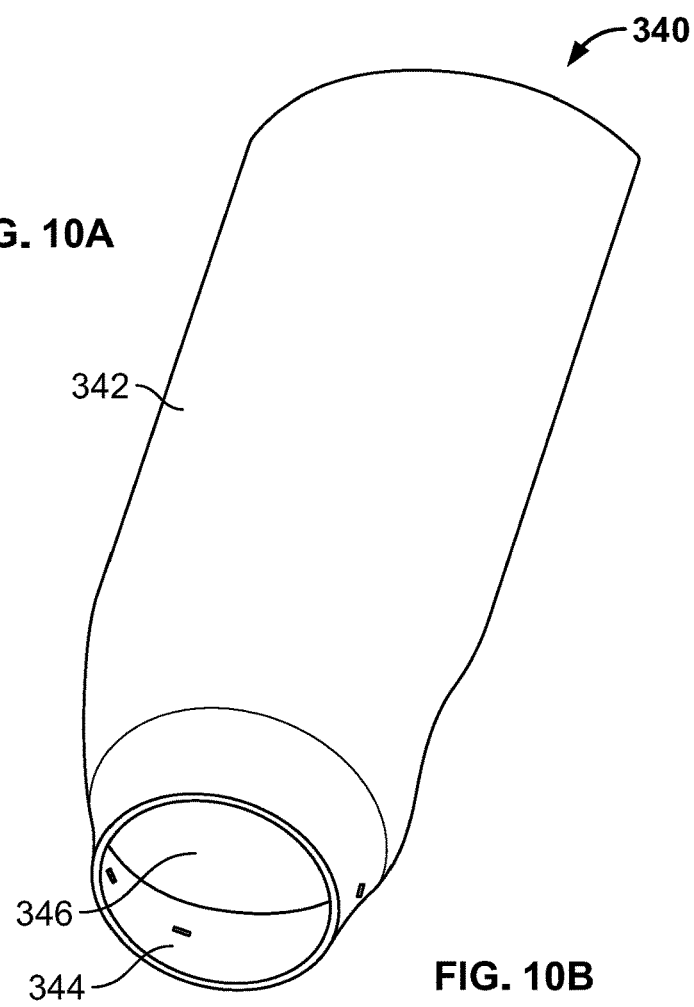

Filamentary receiving component 340, as shown in FIGS. 10A and 10B, is similar to filamentary receiving component 120 and 220 in that it is made from filamentary material and includes a first portion 344 and second portion 342. Moreover, first portion 344 has an opening 346 extending therethrough and second portion 342 extends from an anterior side of first portion 344. However, unlike filamentary receiving components 120 and 220, filamentary component 340 has an annular opening 346 that flares or tapers outwardly in an inferior to superior direction so as to form an annulus with a sidewall that is thinner than the proximal-distal length of second portion. This allows filamentary component 340 to correspondingly engage a prosthesis, such as prosthesis 302, which also tapers along its length. Thus, in the assembly, as shown in FIG. 8, diaphyseal portion 336 extends through opening 346 in first portion 344 of filamentary component 340. The inner surface of first portion 346 bears on body 330 along the tapered outer surface thereof such that the taper of body 330 prohibits second portion 344 from moving proximally beyond a predesignated location on body 330.

In a method for attaching the soft tissue to joint replacement prosthesis 302, a patellar tendon 902 is detached from the tibial tubercle and a proximal section of the tibia is resected at a location along the tibial shaft so that the removed bone includes the tibial tubercle. In addition, prosthesis 302 is assembled by connecting body 330, bearing 320, and hinge component 310. Thereafter, filamentary receiving component 340 is engaged to joint prosthesis 302 by inserting diaphyseal portion 336 through opening 346 so that the inner surface of first portion 344 is brought into communication with a correspondingly tapered outer surface of prosthesis 302. Implant 302 is then connected to the bone via connection portion 338.

Once assembly 300 is mounted to the tibia, soft tissue is secured to joint replacement prosthesis 302 via filamentary device 340. In order to re-secure the detached patellar tendon 902, the patellar tendon 902 is sewn to a posterior side of second portion 342, as depicted in FIG. 8. Moreover, a muscle 904, such as the medial gastrocnemius may be sewn to an anterior side of second portion 342 of filamentary component 340 via suture or wire. In addition, a suture 906 may be threaded through openings 332 and passed through tendon 902, first portion 342 of filamentary component 340, and muscle 904. Thus, this configuration allows for a traditional connection to implant 302 via openings 332 and also allows for the soft tissue 902, 904 to grow into filamentary component 340 thereby providing a strong long term connection. Thus, filamentary component 340 provides a soft tissue ingrowth structure to prosthesis 302.

Figure 11:
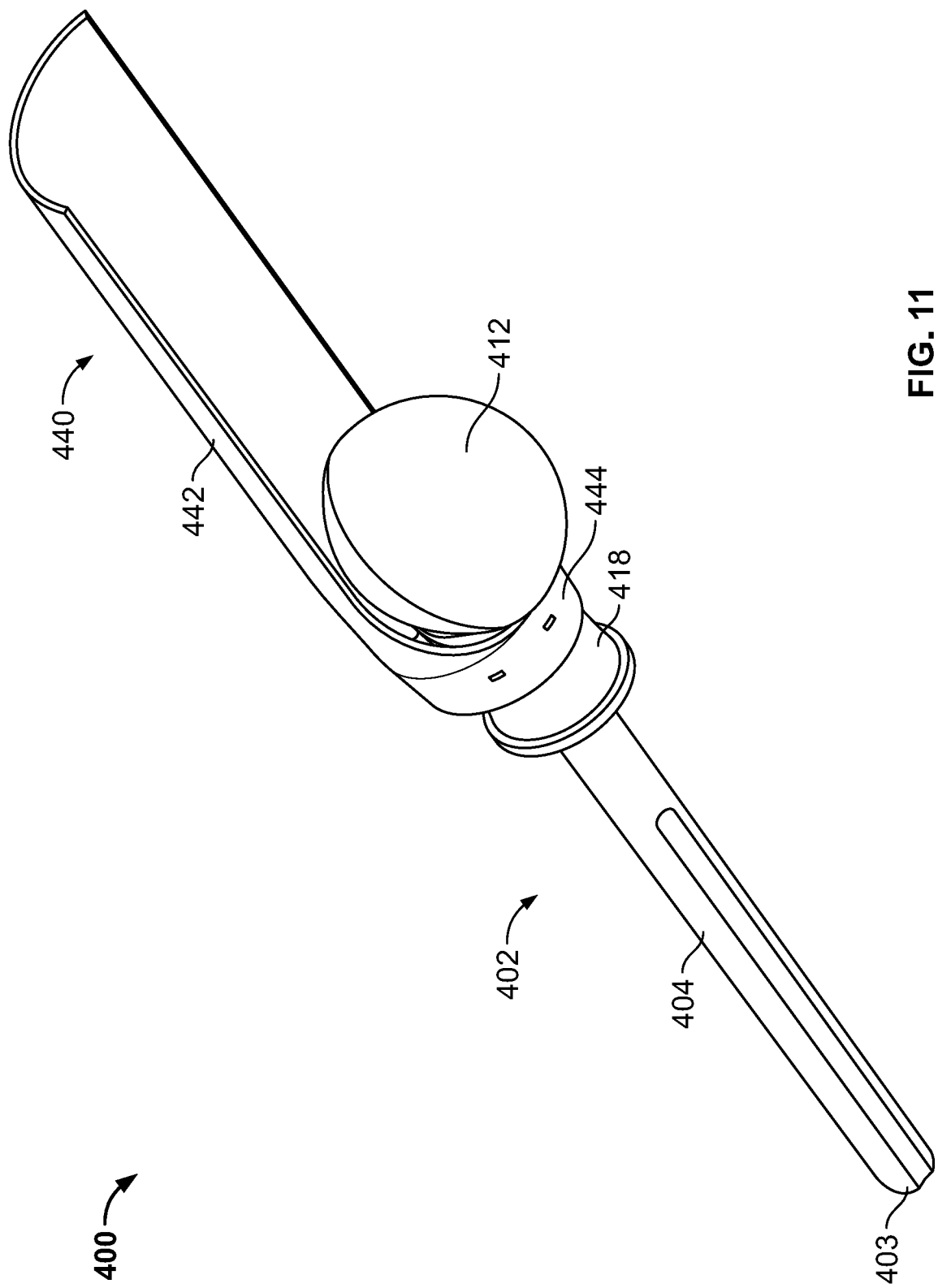
FIG. 11 is a side perspective view of a joint replacement assembly according to yet another embodiment of the present disclosure.

FIG. 11 depicts a joint replacement assembly 400 according to yet another embodiment of the present disclosure. Joint replacement assembly 400 generally includes a joint replacement prosthesis 402 and a filamentary receiving component or filamentary fixation device 440. Joint replacement prosthesis 402 is a humeral joint prosthesis. Thus, as should be understood, the concepts described above with regard to the tibial prostheses embodiments may also be applied to other long bones and joints, such as the humerus and shoulder joint in this embodiment. It should also be understood that the same concepts could also apply to a joint prosthesis for proximal femur and hip joint, for example. Such a hip joint prosthesis would be similarly configured to prosthesis 402 in that it would include an intramedullary stem and a ball joint portion at an end thereof.

Prosthesis 402 comprises a proximal end remote from a distal end. The proximal end includes a head portion 412 that includes a bearing surface that articulates with a glenoid component (not shown) when used in a total should replacement system. Head 412 is connected to a body element 418 which connects to a stem portion 404. Stem portion 404 comprises a tip portion 403 that is adapted to be inserted into an intramedullary canal of a proximal humerus such that stem portion 404 is located within the intramedullary canal thereof. Body element 418 is preferably conically tapered so as to correspond to a taper of an opening of filamentary component 440, as described below. Filamentary receiving component 440 is the same as filamentary receiving component 340 and may be used similarly. In this regard, stem 404 is inserted through an opening in a first portion 444 of filamentary component 440 so that filamentary component 440 bears on body 418 and is retained by corresponding tapers. Additionally, a first portion 442 extends superiorly beyond head element 412. Moreover, a tendon, such as one or all of the tendons of the rotator cuff, may be connected to first portion of filamentary device 440 via suture or wire. In this regard, tissue may grow into first portion 442 to provide long term fixation thereof to prosthesis 402.

Figure 12:
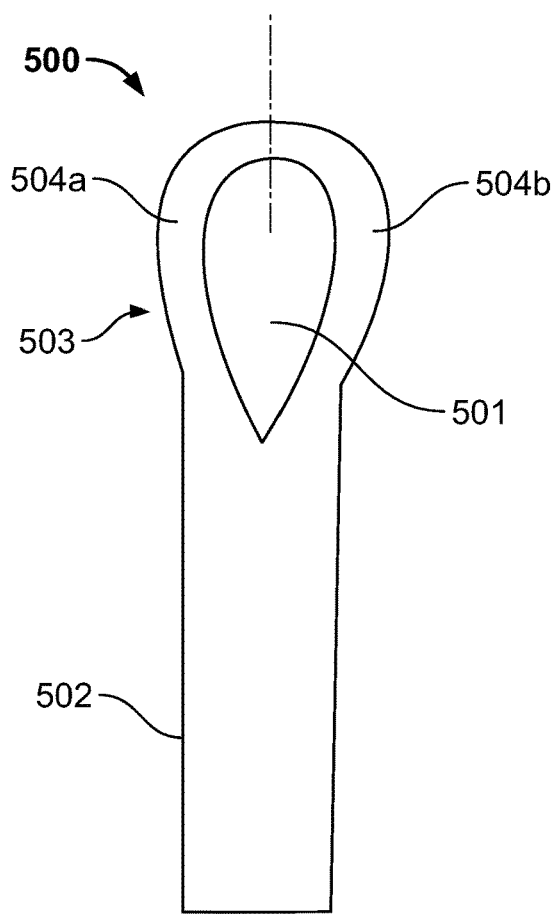
FIG. 12 is a front perspective view of a tissue attachment structure according to an even further embodiment of the present disclosure.

FIG. 12 depicts a front perspective view of an alternative filamentary fixation device 500 configured for use with a joint replacement prosthesis or a joint replacement assembly, according to at least some embodiments disclosed herein. Filamentary device 500 comprises a hoop structure 503 and an opening 501 located within hoop structure 503. Hoop structure 503 is defined by arm members 504a and 504b. Such arm members 504a-b, as shown, are connected together to form hoop structure 503. However, arm members 504a-b are preferably provided disconnected so that they may be tied together or otherwise connected during a procedure, such as about a stem boss 104 and keels 112 or about stem 336 or 403, for example. Moreover, arm members 504a-b may be each comprised of single or double strands of filament such that they have an appearance of shoelaces. This differs from first portion of filamentary device 120 in that when device 500 is connected to prosthesis 102, its footprint relative to baseplate 106 is much smaller than that of filamentary device 120. This allows hoop structure to be trapped between bone and a prosthesis or between components of a prosthesis, as described above, while having a low profile so as to not interfere with direct contact between the bone and prosthesis or prosthesis and prosthesis.

FIGS. 14A-14E depict a joint replacement assembly 600 according to yet another embodiment of the disclosure. Joint replacement assembly 600 is similar to joint replacement assembly 300 in that it includes a joint prosthesis 602 similar to joint prosthesis 302. In this regard, joint prosthesis 602 includes a diaphyseal portion 605 with a connection feature 604 configured to connect to a resected portion of a tibial shaft and a metaphyseal portion 634 configured to interface/articulate with another joint prosthesis, such as a femoral prosthesis (not shown). In the particular embodiment depicted, metaphyseal portion is particularly configured to form a hinged connection with a femoral component. In this regard, metaphyseal portion includes a tray region 642 for a tibial insert (not shown) and an elongate opening 641 extending therein for a stem of an axle assembly (not shown). Exemplary components that can be used in conjunction with assembly 600, and other tibial assemblies described herein, can be found in U.S. Pub. No. 2017/0035572, the disclosure of which is hereby incorporated by reference herein in its entirety.

However, assembly 600 differs in that it also includes a filamentary fixation device 640 and a connectable sleeve 662. Moreover, joint prosthesis 602 is configured to receive filamentary fixation device 640 and connectable sleeve 662. In this regard, metaphyseal portion 634 includes openings or elongate slots 658 which extend through metaphyseal portion 634 in an anteroposterior direction and are positioned at opposite lateral and medial sides of a longitudinal axis of prosthesis 602. Such elongate slots 658 have their longitudinal length extending in a generally superior-inferior direction. This elongate configuration corresponds to a flat geometry of filamentary fixation device 640, as described below.

Figure 14A:
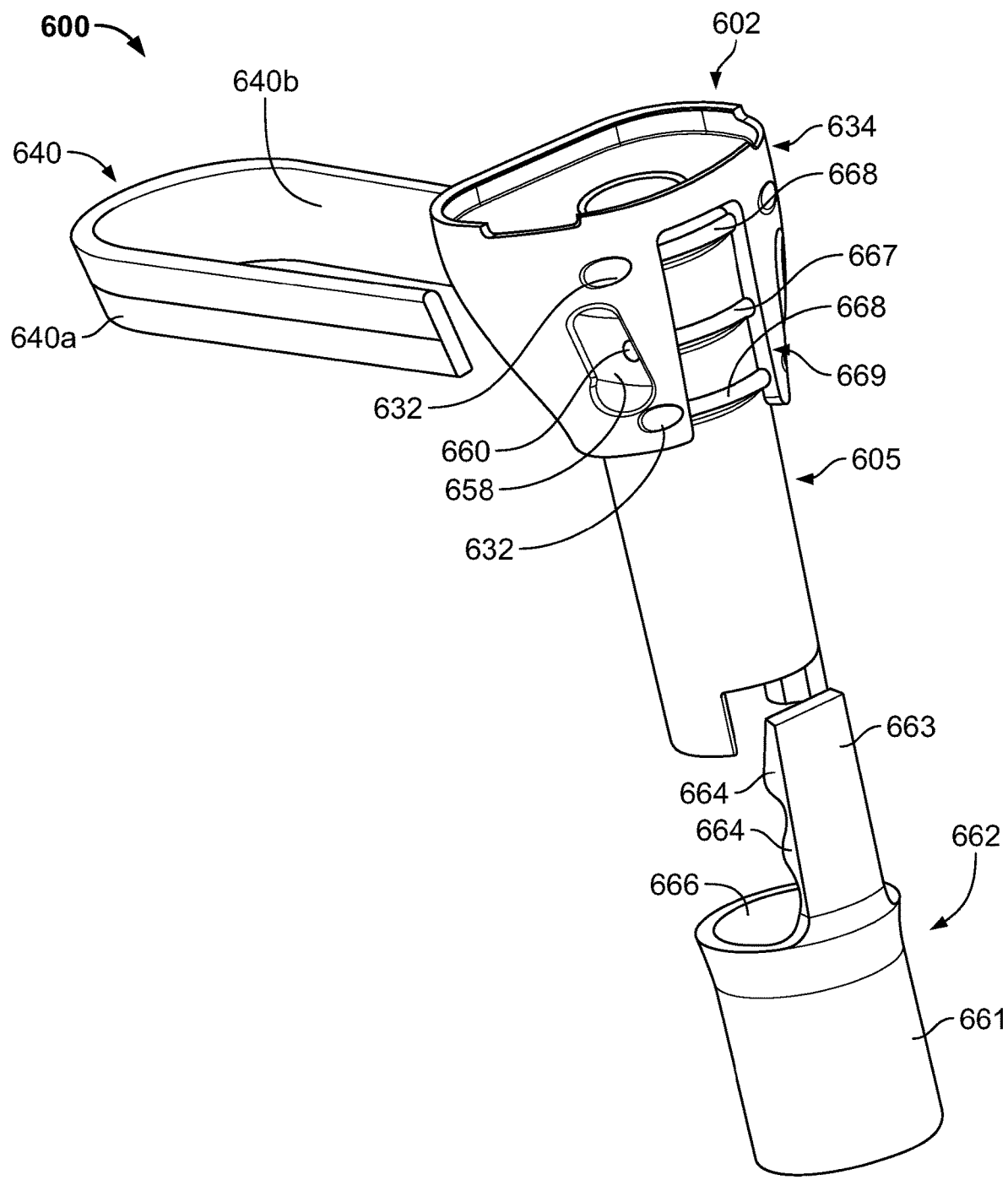
FIG. 14A is an exploded view of a joint replacement assembly according to an even further embodiment of the present disclosure.
Figure 14B:
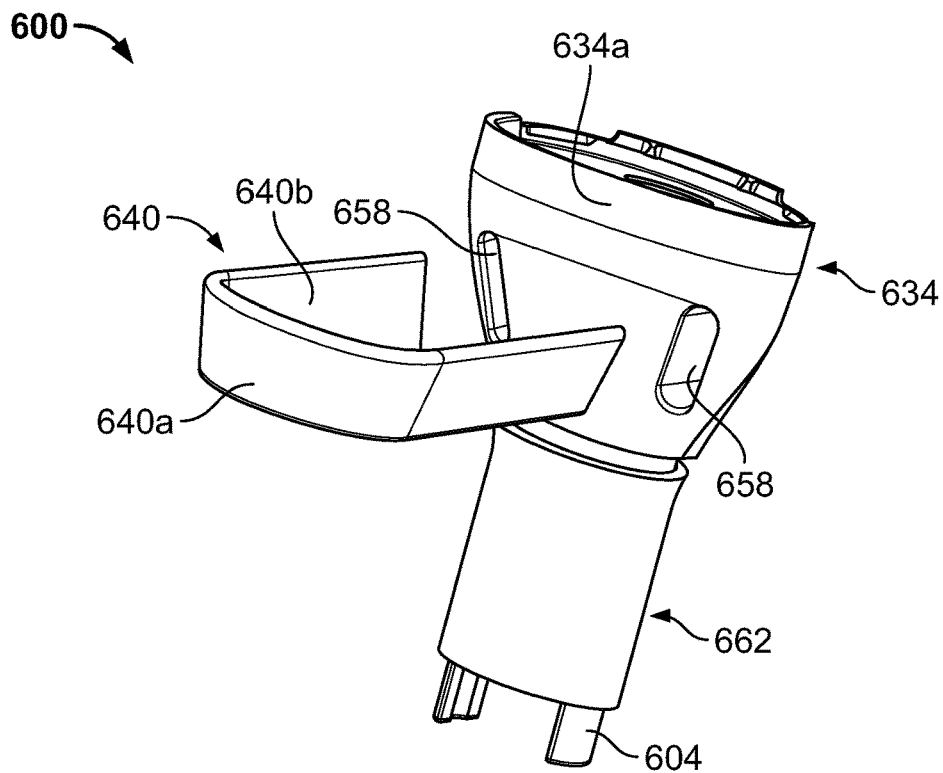
FIG. 14B is a rear perspective view of the joint replacement assembly of FIG. 14A in a first configuration.
Figure 14C:
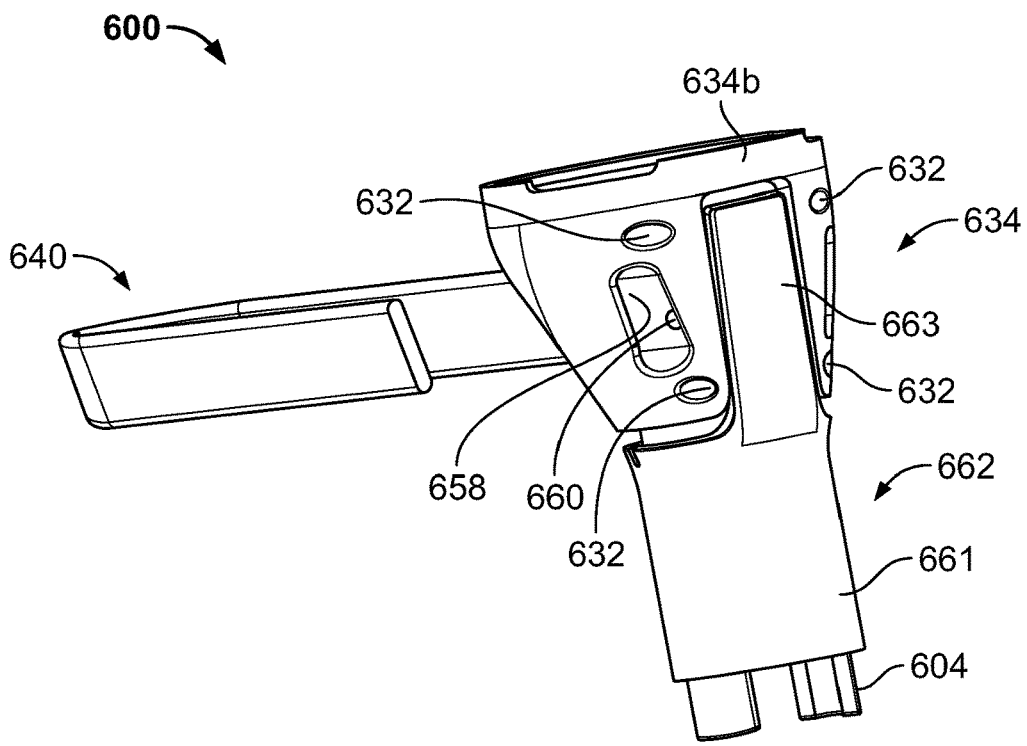
FIG. 14C is a front perspective view of the joint replacement assembly of FIG. 14A in the first configuration.
Figure 14D:
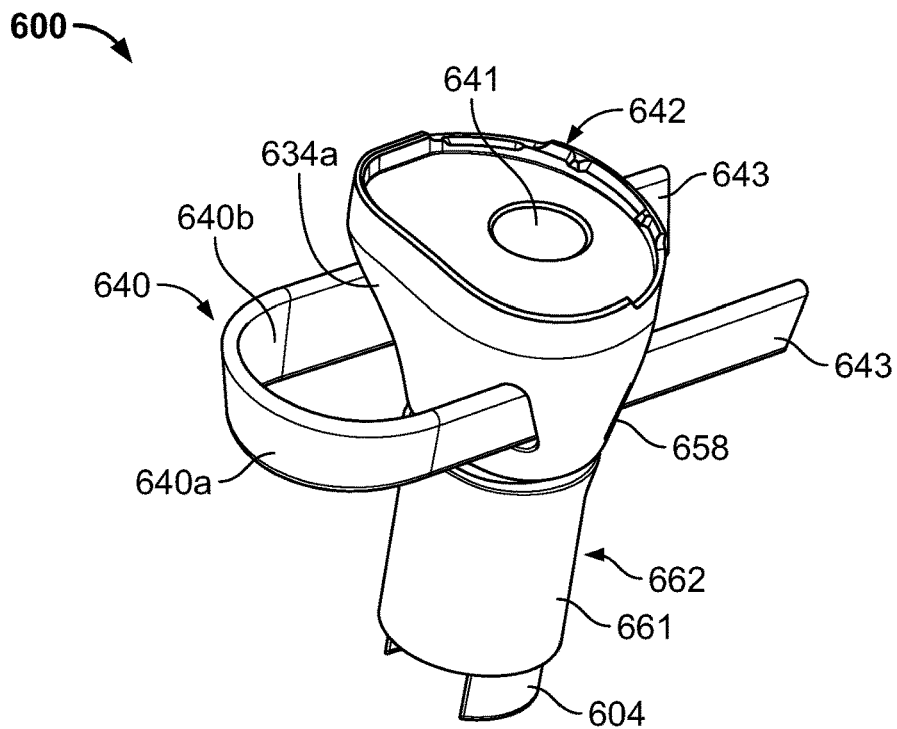
FIG. 14D is a top perspective view of the joint replacement assembly of FIG. 14A in a second configuration.
Figure 14E:
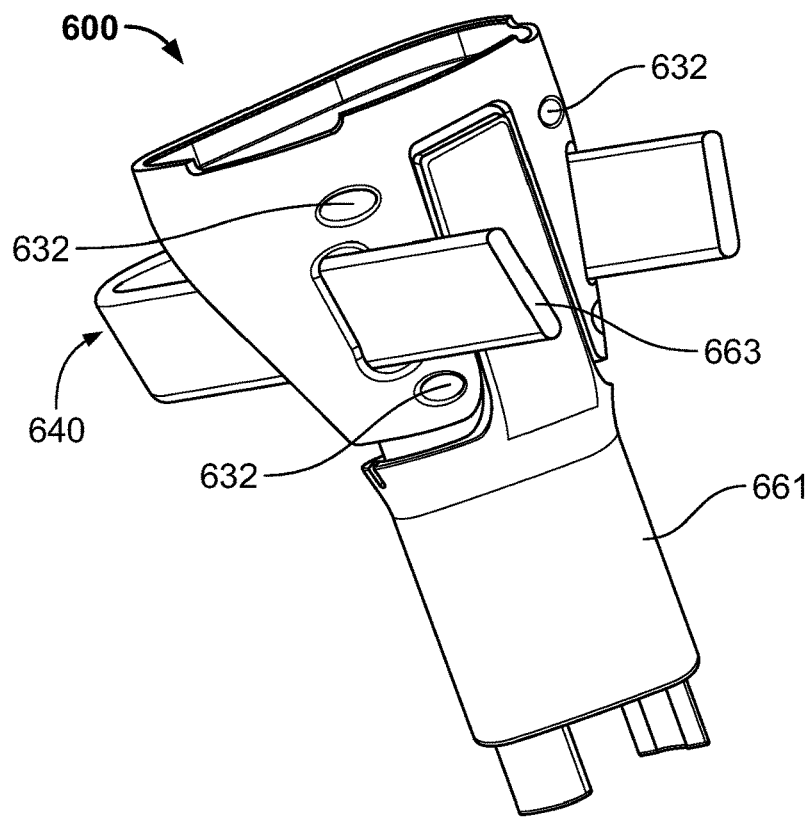
FIG. 14E is a front perspective view of the joint replacement assembly of FIG. 14A in a second configuration.

Metaphyseal portion 634 also includes one or more openings 632 located at an anterior side 634b of prosthesis 602 and extends entirely through prosthesis 602 in a lateral-medial direction. Another opening 660 similarly extends through prosthesis 602 in a lateral-medial direction. In addition, opening 660 intersects elongate slots 658 so as to be in communication therewith, as best shown in FIG. 14A. The intersection of opening 660 with elongate slots 658 allows for a suture or the like to be threaded through filamentary fixation device 640 while disposed in slots 658 and through opening 660 in order to help retain device 640 in a connected state with prosthesis 602.

As mentioned above, prosthesis 602 is also configured to receive sleeve 662. In this regard, diaphyseal portion 605 is conically tapered so as to accommodate sleeve 662 in a taper lock configuration. In addition, metaphyseal portion 634 includes an anterior recess 669 that extends into the anterior face of metaphyseal portion 634. Anterior recess 669 intersects or communicates with openings 632 and 660 to form longitudinal grooves 667 and 668 that are located within the perimeter of recess 669.

Sleeve 662, as best shown in FIG. 14A, includes a ring or cylindrical portion 661 and a tab portion or ingrowth portion 663 extending superiorly therefrom. Ring portion 661 has an opening 666 extending therethrough and is correspondingly tapered relative to portion 605, as indicated above. Also, as mentioned above, tab portion 663 includes projections 664 which extend posteriorly for communication with grooves 667 and/or 668. In this regard, projections 664 may have a concave surface (not shown) that extends laterally-medially to form a groove that corresponds to that of grooves 667 and 668. Thus, when tab portion 663 is positioned within anterior recess 669, projections 664 mate with grooves 667/668 so that the concave surfaces of projections 664 and grooves 667/668 together form cylindrical channels extending through prosthesis 602. Preferably when tab portion 663 is received within recess 669, an outer surface thereof is flush with an outer surface of prosthesis 602. Preferably, tab portion 663 of sleeve 662 is made of a porous material, such as titanium foam, to support tissue ingrowth. For example, an exterior surface opposite projections 664 may be porous while projections 664 may be made from a solid metal material. Such configuration may be made via an additive manufacturing process so as to form a unitary structure. In addition, ring portion 661 may also be made of the same porous material or conversely a solid structure. Although the embodiment depicted includes a taper-lock mechanism to connect sleeve 662 to prosthesis 602, other locking mechanisms are contemplated. For example, one or more threaded fasteners may connect ring portion 661 to diaphyseal portion 605.

Filamentary fixation device 640 is similar to filamentary fixation device 120 in that it is made from a filamentary material that may be a knitted or woven material, a non-woven material, or a combination thereof. However, filamentary fixation device 640 is an elongate flat strip of filamentary material that, when initially connected to prosthesis 602, is folded over so that it resembles "U" shape with an inner surface 640a and an outer surface 640b.

Thus, as assembled, terminal ends 643 of filamentary fixation device 640 are threaded through elongate slots 658 in a posterior to an anterior direction (see FIGS. 14D and 14E) so that inner surface 640b of the U-shaped construct engages a posterior side 634a of metaphyseal portion 634. The flat profile of filamentary fixation device 640 helps it conform to prosthesis 602 to provide a low profile. Thus, filamentary fixation device 640 has free ends 643 that can wrap around the anterior outer surface 634a of metaphyseal portion 634 with the ends 643 of filamentary fixation device 640 going through respective openings 658. A suture (not shown) may be passed through suture opening 660 and fixation device 640 at both the lateral and medial sides of prosthesis 602 to further secure filamentary fixation device 640 and to prosthesis 602 and to prevent device 640 from backing out of openings.

Also, as assembled, ring portion 661 of sleeve 662 receives diaphyseal portion 605 so that tab portion 663 extends superiorly and so that an outer surface of portion 605 interferes with an inner surface of ring portion 661 to form a taper lock. Projections 664 of tab portion 663 are positioned in communication with grooves 667/668 of prosthesis 602 so as to partially define openings 632 and 660. This allows sutures to be threaded through openings 632 and 660, as desired, to secure soft tissue and filamentary fixation device 640 to prosthesis 602.

Furthermore, filamentary fixation device 640 may arrive to the operating theater pre-loaded to prosthesis 602 so that its free ends 643 extend in a posterior to anterior direction through openings 658. The operator may optionally thread a suture through device 640 and through opening 660 in order to further secure device 640 to prosthesis. Alternatively, such suture may be pre-threaded to device 640 and prosthesis 602 before arriving to the operating theater.

In a method for attaching the soft tissue to joint replacement prosthesis 602, a similar method as shown in FIG. 8 is used with the joint replacement assembly 600 depicted in FIGS. 14A-14E. In this regard, a patellar tendon 902 is detached from the tibial tubercle and a proximal section of the tibia is resected at a location along the tibial shaft so that the removed bone includes the tibial tubercle. In addition, prosthesis 602 is assembled by connecting sleeve 662 thereto. However, sleeve 662 may be pre-assembled prior to delivery to the operating theater. Thereafter, filamentary fixation device 640 is engaged to joint prosthesis 602 by inserting ends 643 of filamentary fixation device 640 into openings 658 so that inner surface 640b is brought into communication with a posterior surface 634a of metaphyseal portion 634. Prosthesis 602 is then connected to the bone via a connection portion 604 and/or intramedullary stem (not shown) at the distal end of diaphyseal portion 604.

Once assembly 600 is mounted to the tibia, soft tissue is secured to joint replacement prosthesis 602 via filamentary device 640. In order to re-secure the detached patellar tendon 902, the patellar tendon 902 is positioned adjacent tab portion 663 of sleeve 662 so that tendon 902 contacts the porous structure thereof. Free ends 643 of filamentary device 640 are then wrapped tightly about the tendon 902 (see e.g., FIG. 8) and sewn thereto such that tendon 902 is sandwiched between porous sleeve 662 and filamentary fixation device 640. This allows tissue to grow from tendon 902 into the porous sleeve 662 and the porous, mesh-like structure of filamentary device 640. Moreover, a muscle, such as muscle 904 in FIG. 8 may be sewn to the fixation device 640 at an anterior side of prosthesis 602. In addition, a suture or cerclage wire may be threaded through openings 632 and/or 660 and passed through tendon 902 and/or muscle 904. Thus, this configuration allows for a traditional connection to implant 602 via openings 632 and 660 and also allows for the soft tissue 902, 904 to grow into filamentary component 640 thereby providing a strong initial and long-term connection. Thus, filamentary component 640 provides a soft tissue ingrowth structure to prosthesis 602.

Figure 15A:
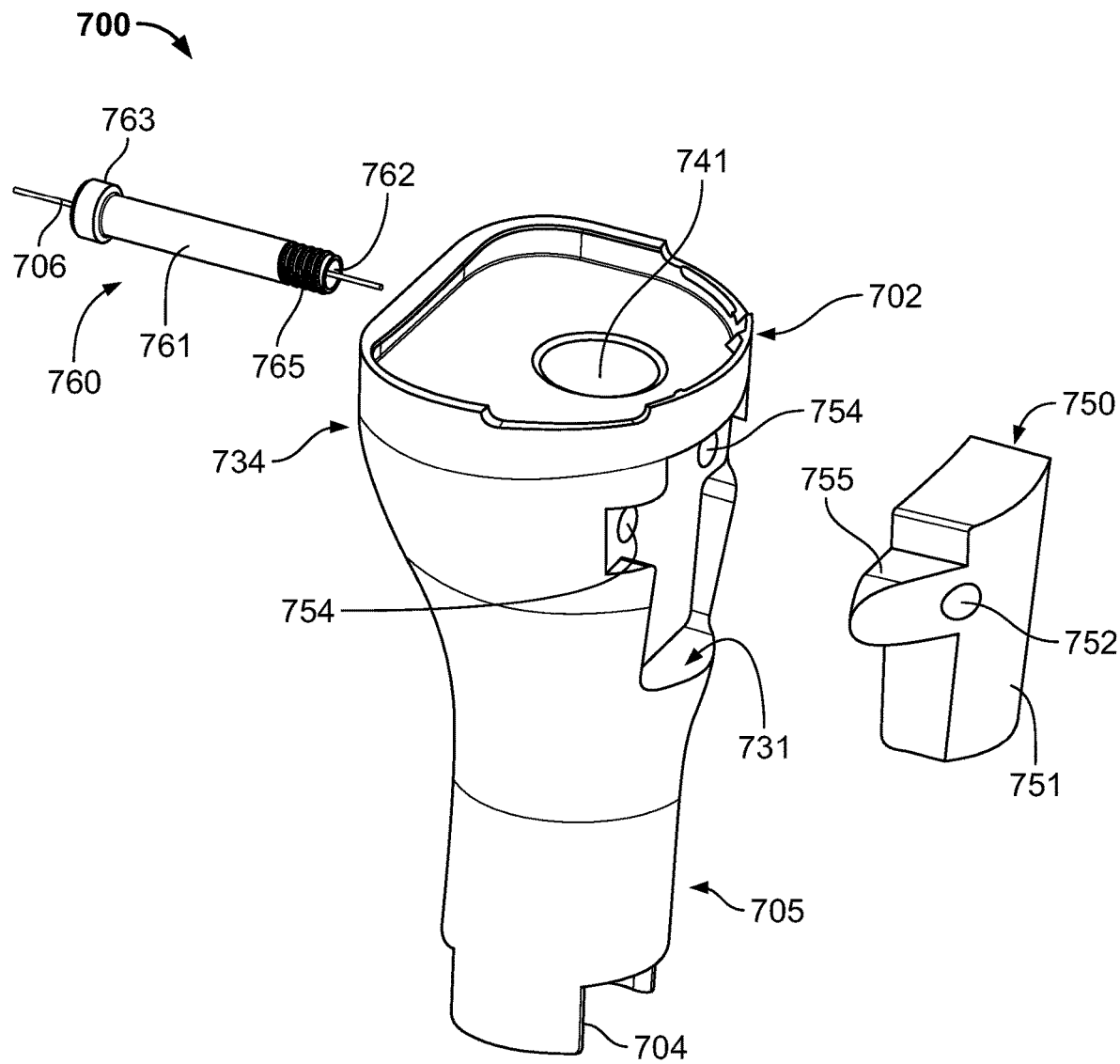
FIG. 15A is an exploded view of a joint replacement assembly according to another embodiment of the present disclosure.
Figure 15B:
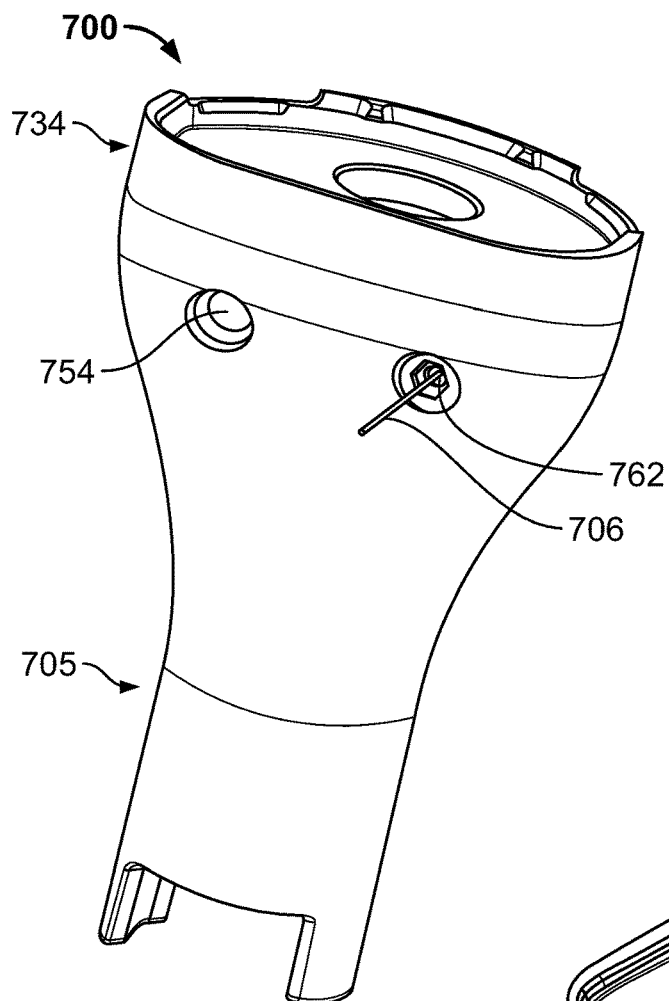
FIG. 15B is a rear perspective view of the joint replacement assembly of FIG. 15A.
Figure 15C:
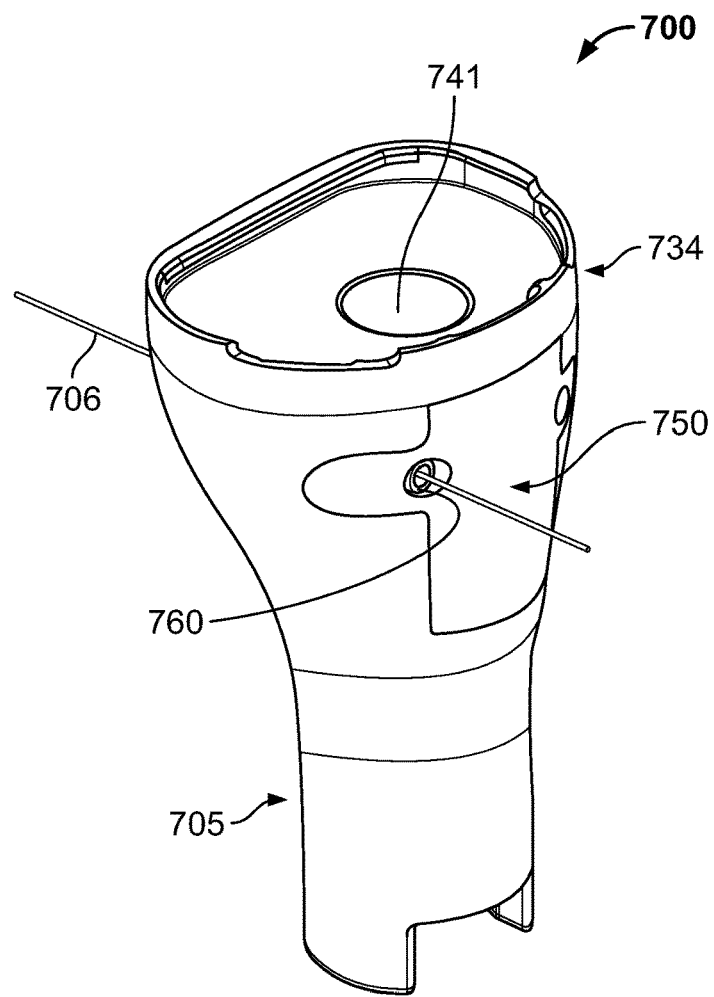
FIG. 15C is a front perspective view of the joint replacement assembly of FIG. 15A.

Joint replacement assembly 700, as shown in FIGS. 15A-15C, is yet another embodiment of the disclosure and generally includes a joint prosthesis 702, cannulated screws, 760 and a connection plate or ingrowth plate 750. Joint prosthesis 702 is similar to prosthesis 302 in that it includes a metaphyseal portion 734 configured for connection to another joint prosthesis, such as a femoral component, and a diaphyseal portion 705 with a connection feature 704 that allows prosthesis 702 to be connected to a resected portion of a tibial shaft.

Metaphyseal portion 734 is connected to a proximal end of diaphyseal portion 705 so that prosthesis 702 tapers outwardly in a distal to proximal direction. Metaphyseal portion 734 includes one or more openings 754 that extend entirely through prosthesis 702 in an anteroposterior direction and that are each configured to receive a cannulated screw 760. Metaphyseal portion 734 also includes a recessed portion 731 that matches the shape and size of plate 750, as described in more detail below.

Cannulated screws 760 have a shaft 761, a head 763, and a through-opening 762 extending through the length of screw 760. The shaft 761 is generally cylindrical and comprises the majority of the screw 760. The distal end of screw 760 includes a threaded portion 765. Screw 760 is cannulated so that sutures 706 can be threaded through the length of screw 760. This allows screws 760 to be inserted into openings 754 so that through-opening 762 of each screw 760 provides a passage for a suture through prosthesis 702. The threaded portion 765 of screw 760 is configured to threadedly engage threaded openings 752 in plate so as to secure plate 750 to prosthesis 702, as described below.

Figure 17:
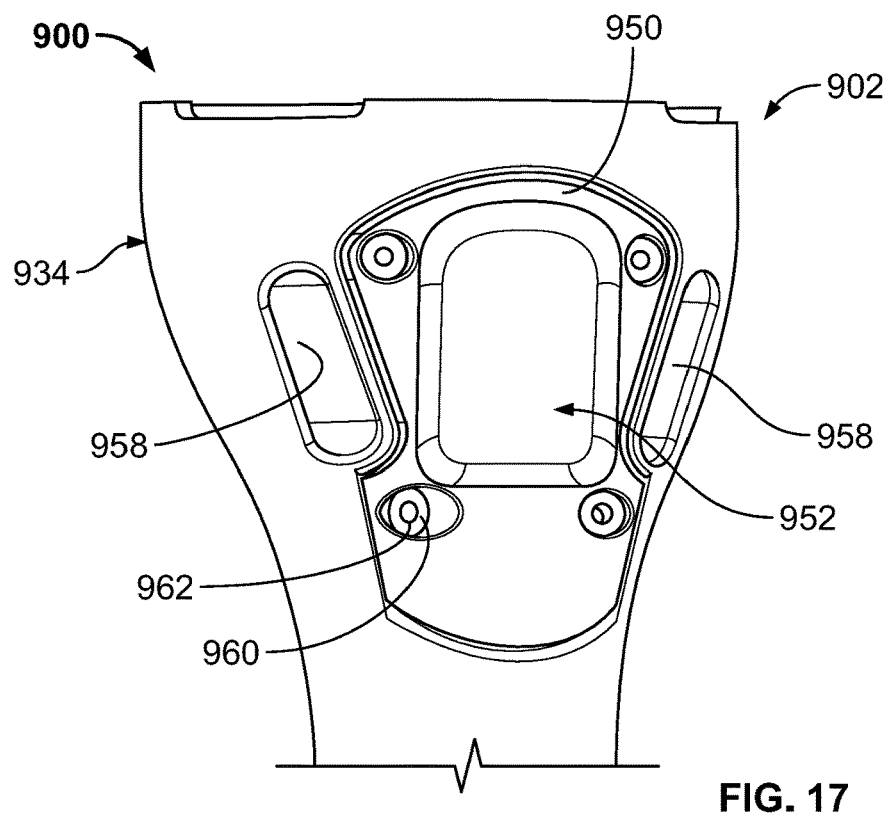
FIG. 17 is a front perspective view of a joint replacement assembly according to a still further embodiment of the present disclosure.

In the embodiment shown, plate 750 has a "T" like shape, in which plate 750 has a body 751 and two projections or wings 755 extending from body 751 in a lateral-medial direction. Plate 750 further includes threaded openings 752 that extend through the thickness of plate 750 and correspond to the location of openings 754 in prosthesis 702 such that when plate 750 is inserted into recess 731, openings 752 and 754 align. Openings 752 are threaded to so that screws 760 can secure plate 750 to prosthesis 702. Plate 750 is preferably composed of a porous material, such as titanium foam, that supports tissue in-growth. However, openings 752 may have a solid metallic structure to provide sufficient strength for a threaded connection with screws 760. As mentioned previously, plate 750 has openings 752 with threads to receive screw 760. As seen in FIG. 17, openings 752 appear to be where the body 751 of plate 750 meets projections 755. However, openings 752 can be located anywhere on plate 750 so long as openings 754 on body 730 correspond. However, it is preferable that openings 754 and openings 752 are located at respective lateral and medial sides of a longitudinal axis of prosthesis 702 so that a suture or the like can be passed from one side of axis to another to secure soft tissue to prosthesis 702. Moreover, plate 750 does not have to be limited to a "T" shape. For example, plate could just be rectangular and not include projections 755. However, in such embodiment, plate 750 would have a larger lateral-medial width than the plate depicted. Other exemplary configurations of plates are describe in more detail below.

In a method of using assembly 700 to connect a patellar tendon thereto, plate 750 may be connected to prosthesis 702 via cannulated screws 760. This may be done in the operating theater or prior to delivery to the operating theater. Prosthesis 702 may then be connected to a proximal end of a resected tibia and the patellar tendon positioned adjacent porous plate 750. Suture or wire may then be threaded through cannulated screws 760 about metaphyseal portion 734 and through and/or about the patellar tendon so as to secure the patellar tendon against porous plate 750 so that tissue from the tendon can grow into its porous structure. Thus, while assembly 700 may not include a filamentary fixation device that would allow for tissue growth therein like that of assembly 600, assembly 700 still allows for tissue in-growth into the porous plate 750 at the anterior face of prosthesis 702. Thus, a filamentary device, such as strand of suture or wire, positioned through cannulated screws 760 can help provide immediate fixation, while porous plate 750 facilitates long-term fixation.

However, it is contemplated that assembly 700 can also include a filamentary fixation device to further enhance long term fixation. For example, filamentary fixation device 340 may be slid over diaphyseal portion 705 so that portion 705 is received within opening 346. The patellar tendon may sutured to second portion 342 as described above with respect to FIG. 8. In this regard, the patella 902 may be sandwiched between porous plate 750 and second portion 342 of device 340 so that the soft tissue may grow into bone plate 750 and second portion 342.

Figure 16:
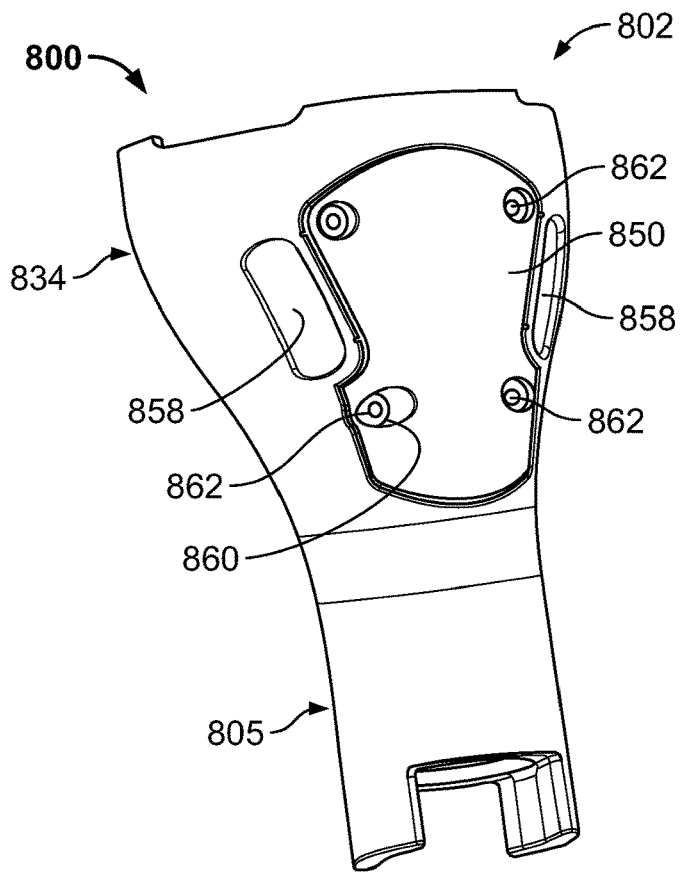
FIG. 16 is a front perspective view of a joint replacement assembly according to yet another embodiment of the present disclosure.

Joint replacement assembly 800, as shown in FIG. 16, depicts a further joint replacement assembly embodiment of the present disclosure. Joint replacement assembly 800 is similar to assemblies 600 and 700. In this regard, assembly 800 includes a joint prosthesis 802, cannulated screws 862, and a connection plate or ingrowth plate 850 that is of a porous material or has a porous exterior surface connectable to the joint prosthesis 802 similar to that of assembly 700. However, unlike assembly 700, four cannulated screws 860 are used to connect plate 850 to prosthesis 802. Thus, it should be understood that two or more cannulated screws 860 may be used to connect a porous plate to an underlying prosthesis. Also, unlike in assembly 700 but similar to assembly 600, prosthesis 802 includes longitudinal slots similar to that of slots 658. This allows filamentary fixation device 640 to be used in assembly 800 to help secure soft tissue thereto as described above. Also, as shown, plate 850 has a rough hour-glass shape which helps occupy as much space as possible between longitudinal slots or through-slots 858 to help ensure contact with soft tissue for growth therein.

Soft tissue is connected to prosthesis 802 similar to that of prosthesis 602 and 702. In this regard, a patellar tendon that has been disconnected from a tibia is positioned against porous plate 850. Filamentary fixation device 640 is threaded through slots 858 and free ends 643 thereof are placed over the tendon and sewn together via suture or wire, as described with respect to assembly 600. In addition, the tendon may be further secured via sutures or wire through cannulated screws 860, as described with respect to assembly 700. Thus, this configuration allows for a connection to implant 802 via the cannulation in screws 860 to provide for a strong immediate connection and also allows for the soft tissue, such as tissue 902, 904 of FIG. 8, to grow into filamentary fixation device 640 and porous plate 850 thereby providing a strong long-term connection.

FIG. 17 depicts another joint replacement assembly 900 similar to that of 800 and is accorded like reference numerals, but within the 900 series of numbers. However, the difference between assembly 800 and 900 is that assembly 900 includes a connection plate or ingrowth plate 950 that is of a porous material or has a porous exterior surface with a depression 952 on its anterior or outer surface. This depression 952 allows a portion of bone, such as a resected tibial tubercle with attached tendon, to be received therein and so that such bone can grow into the porous structure of plate 950. Depression 952 provides a relief for the resected bone with tendon attached thereto to seat at a natural anatomic height relative to the anterior face of prosthesis 902. Thus, the method is identical to that of assembly 800 with the difference being that bone underlying the patella is excised and connected to plate within its anterior depression 952.

FIGS. 18A-18E depict another joint replacement assembly 1000 similar to that of assemblies 800 and 900. In this regard, assembly 1000 includes a joint prosthesis 1002 that includes a metaphyseal portion 1034 and a diaphyseal portion 1005 and is generally constructed as a tibial prosthesis. Moreover, metaphyseal portion 1034 includes a tray region 1042 for a tibial insert, a plurality of through-holes 1054, 1056 configured to each receive a cannulated screw, such as screws 860 and 960, an anterior recessed portion 1031 for receipt of an ingrowth plate, such as plates 850 and 950, and through-slots 1058 for receipt of a filamentary fixation device, such as filamentary device 640.

However, through-slots 1058 are differently configured than slots 858 and 958. In this regard, slots 1058 each extend through posterior and anterior sides of prosthesis 1002 such that each slot 1058 defines an anterior or first aperture 1057a and posterior or second aperture 1057b. The posterior aperture 1057b, as best shown in FIG. 18C, is pill-shaped such that it defines a longitudinal axis 1058b that is parallel to a central axis of prosthesis 1002. The anterior aperture 1057a, as best shown in FIG. 18A, is triangular, as illustrated by the superimposed right triangle 1058a. However, the apices of the triangle formed by anterior aperture 1057a are rounded rather than pointed. In addition, each slot 1058 is defined along its anteroposterior traversal by first and second opposing sidewalls 1051a-b. The first sidewall 1051a has a constant superior-inferior height along the traversal of each slot 1058 from posterior aperture 1057b to anterior aperture 1057a. However, the second sidewall 1051b gradually shortens in height along the traversal of each slot 1058 from posterior aperture 1057b to anterior aperture 1057b. In addition, first wall 1051a is generally parallel to a central axis 1004 of prosthesis at both the anterior and posterior aperture 1057a-b and also therebetween. However, second wall 1051b, while being substantially parallel to central axis 1004 at the posterior aperture 1057b, gradually tilts away from central axis 1004 as second wall 1051b extends posterior to anterior so that second wall 1051b adjacent the anterior aperture 1057a is canted away from axis 1004 and forms the hypotenuse of the triangular-shaped anterior aperture 1057a. Thus, a plane tangent to second sidewall 1051b intersects central axis 1004. Moreover, in the particular embodiment depicted, second sidewall 1051b also curves inwardly about central axis 1004 in a posterior to anterior direction, as illustrated by the arc line overlay 1053 in FIG. 18B. In other words, second sidewall 1051b follows a curved path so that second sidewall 1051b itself defines a curved surface. However, it is contemplated that second sidewall 1051b may be planar while having other characteristics described above, such as being canted away from central axis 1004. It is also contemplated that both first and second apertures 1057a-b may be triangular.

Figure 18D:
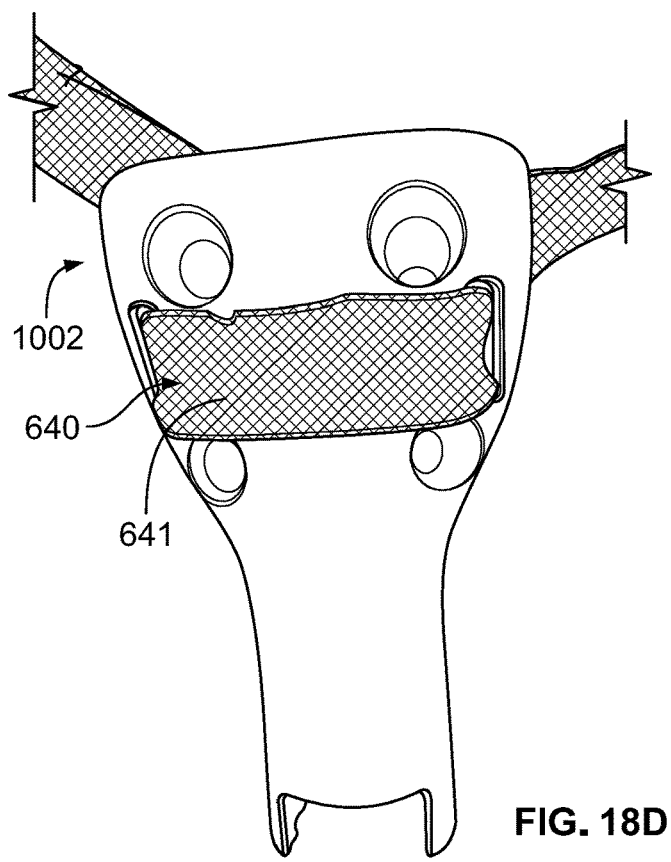
FIG. 18D is a rear perspective view of a joint replacement assembly including the joint replacement prosthesis of FIG. 18A and a filamentary fixation device of FIG. 14A.
Figure 18E:
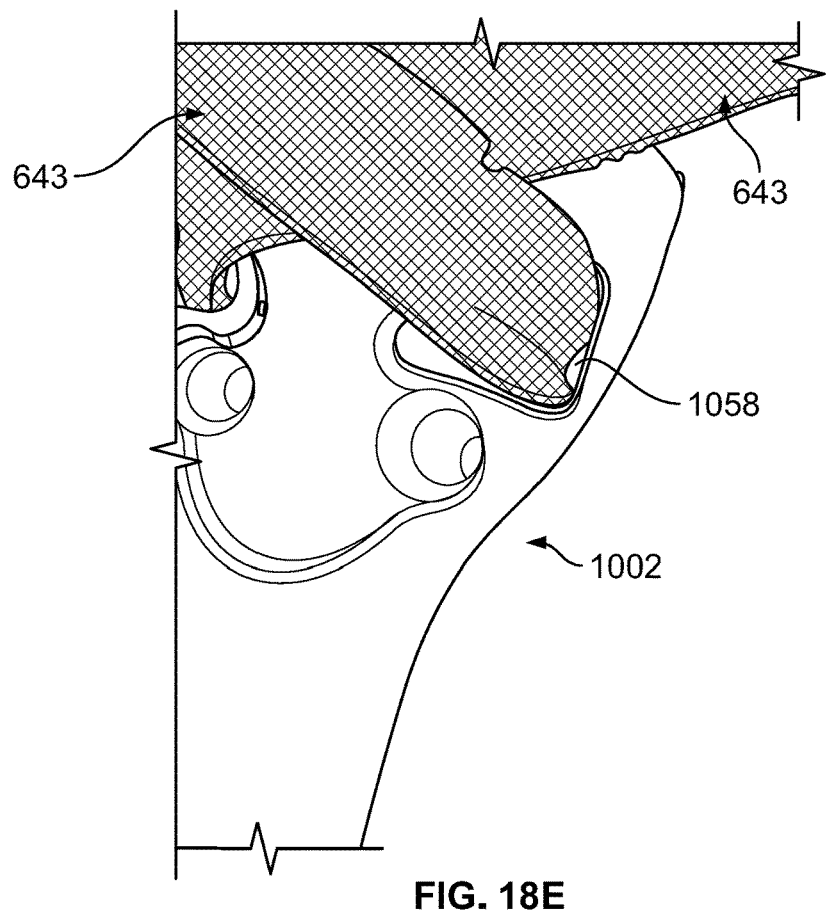
FIG. 18E is a partial front perspective view of the joint replacement assembly of FIG. 18D.

The depicted embodiment allows filamentary fixation device 640 to be threaded through slots 1058 similar to that described above with respect to assemblies 800 and 900 so that a segment 641 of device 640 that spans between slots 1058 conforms to the posterior side of prosthesis 1002 and is pressed flat against the posterior side of prosthesis 1002, as best shown in FIG. 18D. In this regard, the flat configuration of filamentary device 640 and the orientation of slots 1058 so that they form a posterior aperture 1057b that is substantially parallel to the central axis 1004 helps provide a low profile of device 640 at the posterior side of prosthesis 1002 so as to minimize soft tissue irritation while also distributing loads over a broad surface area for durability. In addition, each free end 643 of device 640, as they follow second wall 1051b of their respective apertures 1058, turns so that their axes are no longer horizontal, but instead are angled superiorly so that free ends 643 cross in an X-shaped arrangement, as best shown in FIG. 18E. This arrangement helps redirect free ends 643 so that they do not interfere with each other as they extend over the anterior side of prosthesis 1002 and also help distribute loads applied to filamentary fixation 640 device to walls 1051b. In other words, a patella sewn to filamentary fixation device 640 will have a tendency to be pulled superiorly by the extensor mechanism during normal movement of the knee joint. Thus, loads applied to device 640 via the patella will tend to pull on free ends 640 superiorly. With assembly 1000, when such loads are applied to device 640, free ends 640 will be further compressed to surfaces 1051s which further helps distribute the loads over a broad area to maximize durability of device 640. In addition, the curvature of second surfaces 1051a and their angled orientation helps prevent filamentary device 640 from being bunched up at a superior end of each slot 1058.

Several filamentary fixation devices, such as filamentary fixation devices 120, 220, 340, 500, and 640, are described herein. Such fixation devices may be made by folding over and or tubularizing sheets of synthetic mesh, such as Marlex mesh manufactured by CR Bard, Inc., and then shaping such mesh into the desired form. However, folding over or rolling sheets of mesh material can result in a stiff, bulky structure. In addition, sutures threaded through such structures cut through or rip through edges of the mesh material as the only structure preventing this are the woven fibers of the filamentary material which typically loosely engage the suture.

In order to address some of the existing problems with surgical mesh in extensor mechanism repair, filamentary fixation devices 120, 220, 340, 500, and 640 described herein and other filamentary fixation devices not described herein can be made by layering individual sheets of synthetic mesh/filamentary material and heat sealing/bonding the sheets of material together to form an integrated structure.

Figure 19A:
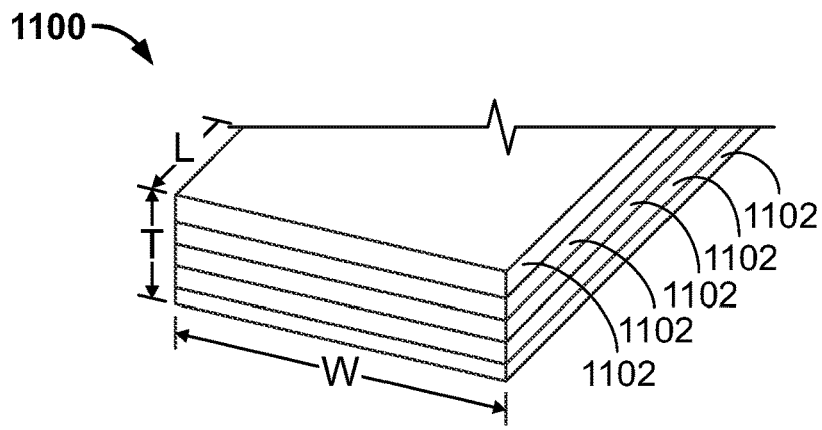
FIG. 19A is a schematic perspective view of a stack of filamentary material.
Figure 19B:
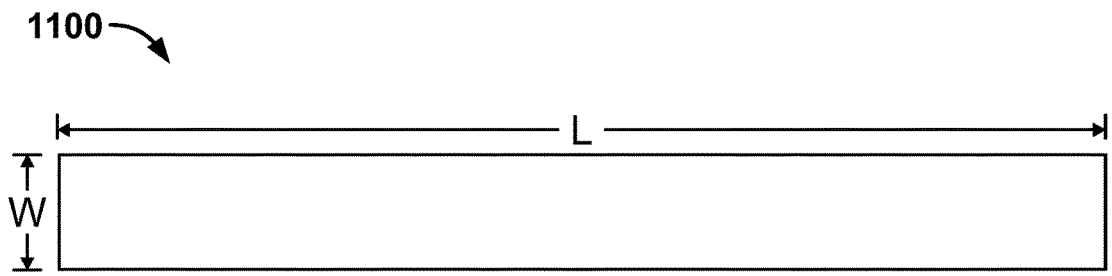
FIG. 19B is a top view of the stack of filamentary material of FIG. 19A.
Figure 19C:
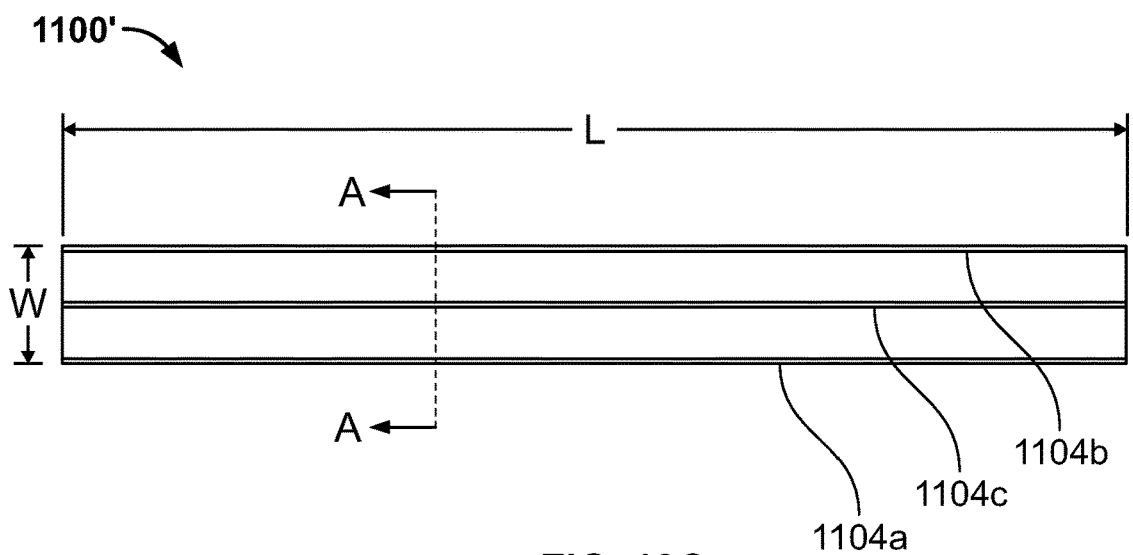
FIG. 19C is a top view of a filamentary fixation device according to a further embodiment of the present disclosure including the filamentary material of FIG. 19A.
Figure 19D:
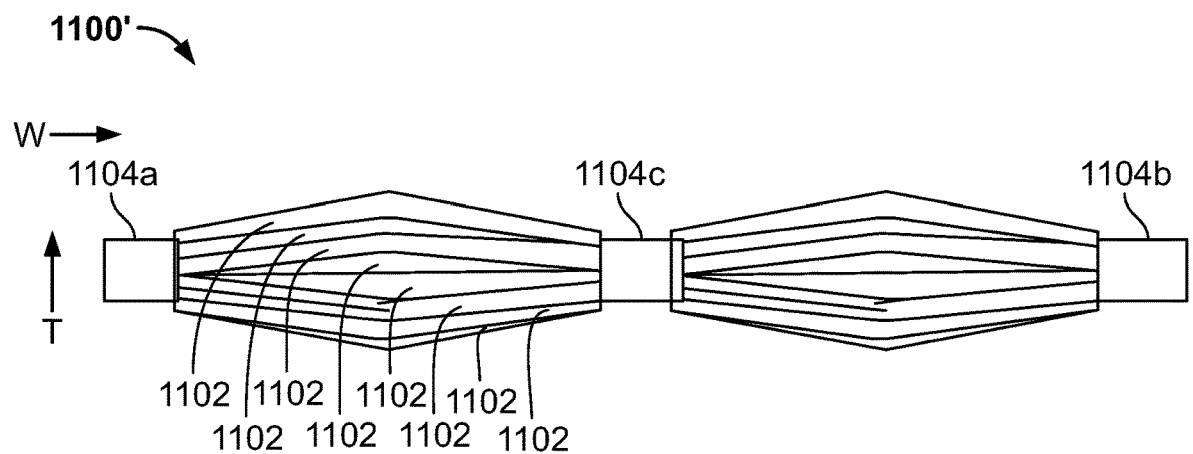
FIGS. 19D and 19E are schematic cross-sectional views taken along line A-A of FIG. 19C.
Figure 19E:
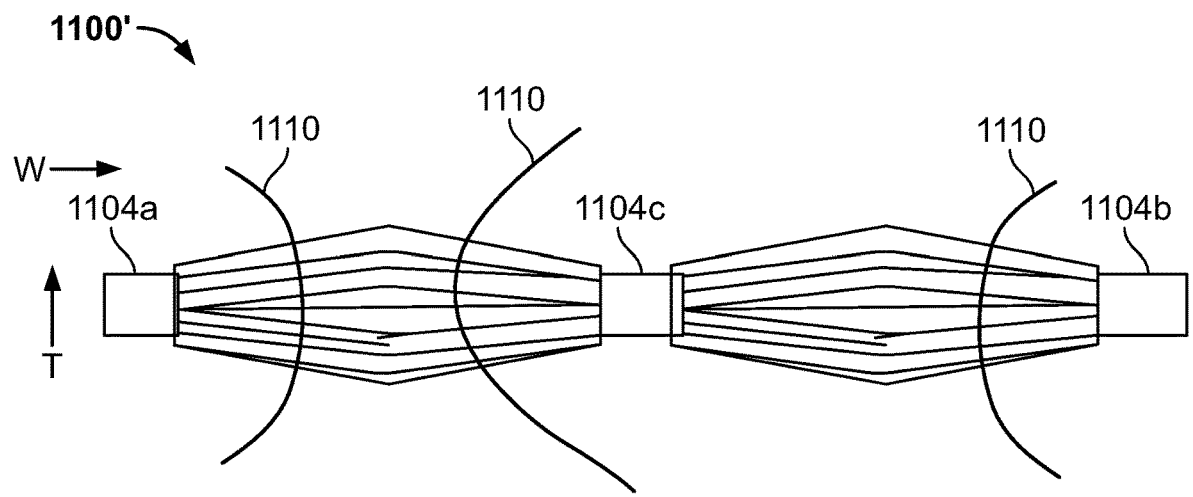

An embodiment of such integrated filamentary fixation structure 1100' is depicted in FIG. 19C-19E. Filamentary fixation device 1100' is similar to filamentary device 640 and, therefore, can be used in the same manner described above. Filamentary fixation device 1100' begins as a plurality of layers 1102 of mesh material that are stacked onto one another to form a construct 1100 having a desired width "W", length "L", and thickness "T", as shown in FIGS. 19A and 19B. In this regard, the construct 1100 can have any number of layers of material, such as 2 to 20, but preferably 8 to 12 layers. The construct 1100 is then heat sealed through its full thickness so that each layer 1102 is connected to an adjacent layer in order to form device 1100'. In some embodiments, large sheets of material may be layered, heat sealed, and then cut to the desired dimensions to form device 1100'. In addition, it is contemplated that other means of connection between layers 1102 is contemplated, such as sonic welding, adhesives, and the like.

As shown in FIG. 19C-19E, filamentary fixation device 1100' includes a plurality of seams 1104 that are formed so that they each extend continuously along the entire length thereof and through the entire thickness thereof. In this regard, the length of each seam 1104 is in a direction of the expected load. Thus, in some circumstances, where the expected load may be multi-directional, it is contemplated that there may be overlapping seams that extend in different directions, such as along both the length and width of device 1100'. In the embodiment depicted, a first and second seam 1104a-b are formed at the side edges of device 1100' and a third seam 1104c is formed down a centerline of device 1100'. In this regard, each layer 1102 is free to move relative to adjacent layers between the seams 1104a-c, as depicted in the cross-sections of FIGS. 19D and 19E. Some embodiments may have more than three continuous seams 1104, such as 4 to 8 seams. Moreover, seams 1104 may be positioned relative to each other at consistent intervals or at differing intervals such that the distance between each seam 1104 differs from one seam to the next.

FIG. 19E illustrates various suture pathways that may be used to connect soft tissue to device 1100'. As shown, a suture may be threaded through each layer of device 1100' between adjacent seams. In this regard, seams act as a structural barrier that helps prevent sutures from cutting entirely through device and helps maintain the sutures in their respective lanes between seams.

Figure 19F:
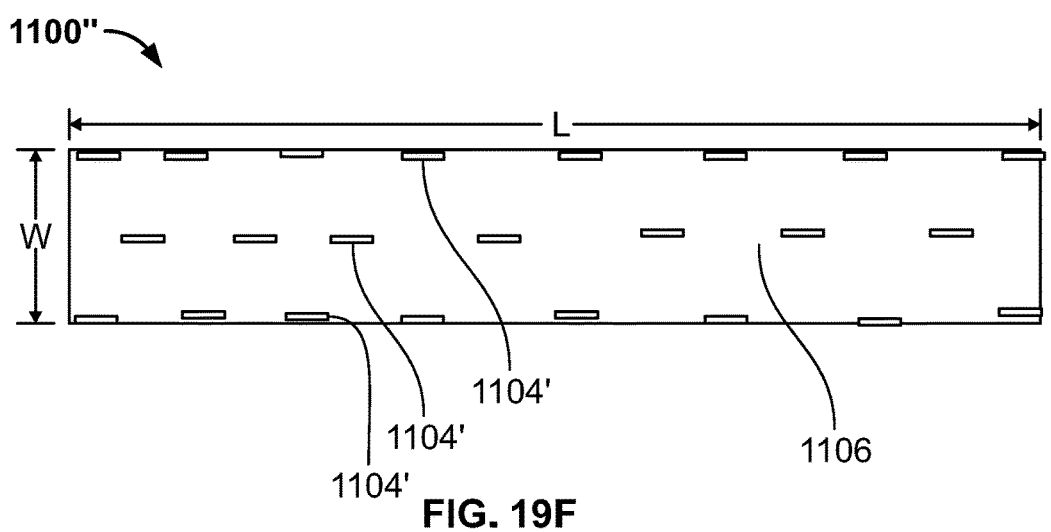
FIG. 19F is a top view of another filamentary fixation device including the stack of filamentary material of FIG. 19A.

FIG. 19F depicts an alternative fixation device 1100". Fixation device 1100" has a plurality of interrupted or discontinuous seams 1104', whereas device 1100' has a plurality of continuous seams 1104. Thus, while each seam 1104' similarly extends along the length of device 1100" and through its full thickness, each seam 1104' is interrupted at predetermined intervals along its length by free segments 1106 which lie along the axis of the seam 1104'. The layers 1102 at the free segments 1106 are not bonded together and, therefore, are free to move relative to each other. Such an interrupted configuration can provide further flexibility over that of device 1100'. It is also contemplated that other devices not shown can have a combination of continuous and interrupted seams. For example, side edges of a filamentary fixation device can be sealed with continuous seams, such as seams 1104a-b, while one or more seams between such side edges are sealed with interrupted seams, such as seams 1104'.

Layered mesh with continuous or interrupted seams 1104, 1104' are advantageous because they allow the overall construction of a filamentary fixation device to have a thinner profile than a typical folded or rolled construction. Moreover, such layered construction provides enhanced flexibility as the overall construct is less bulky. In addition, the interrupted seam 1104' may provide even further flexibility due to free segments 1106, as mentioned above. Even further, layering mesh filamentary material and connecting them via a heat fusion or the like allows the layered construction to be cut and shaped much like a textile material so that the layered construct can take on any of the forms of the herein described filamentary fixation devices.

FIGS. 20A-20F depict further joint replacement assembly 1200 similar to that of assembly 1000. In this regard, assembly 1200 includes a joint prosthesis 1210 that includes a metaphyseal portion 1234 and a diaphyseal portion 1205 and is generally constructed as a tibial prosthesis. Moreover, metaphyseal portion 1234 includes a tray region 1242 for a tibial insert, a plurality of screw openings 1254, 1256 configured to each receive a screw 1260, an anterior recessed portion similar to recessed portion 1031, a connection plate or ingrowth plate 1290 received within such recessed portion, and through-slots or through-openings 1258 for receipt of a filamentary fixation device, such as filamentary devices 640, 1100, 1100', and 1100", for example. Assembly 1200 also includes through-holes 1232 configured to receive sutures or wires, such as cerclage wires, for example.

Figure 20A:
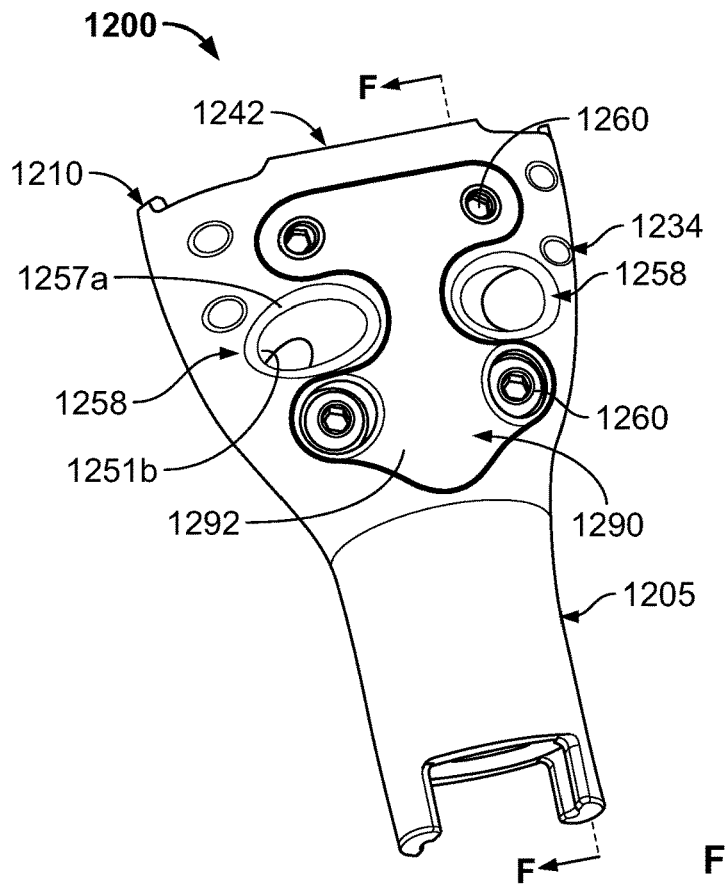
FIG. 20A is a front perspective view of a joint replacement prosthesis including a connection plate and according to an even further embodiment of the present disclosure.
Figure 20B:
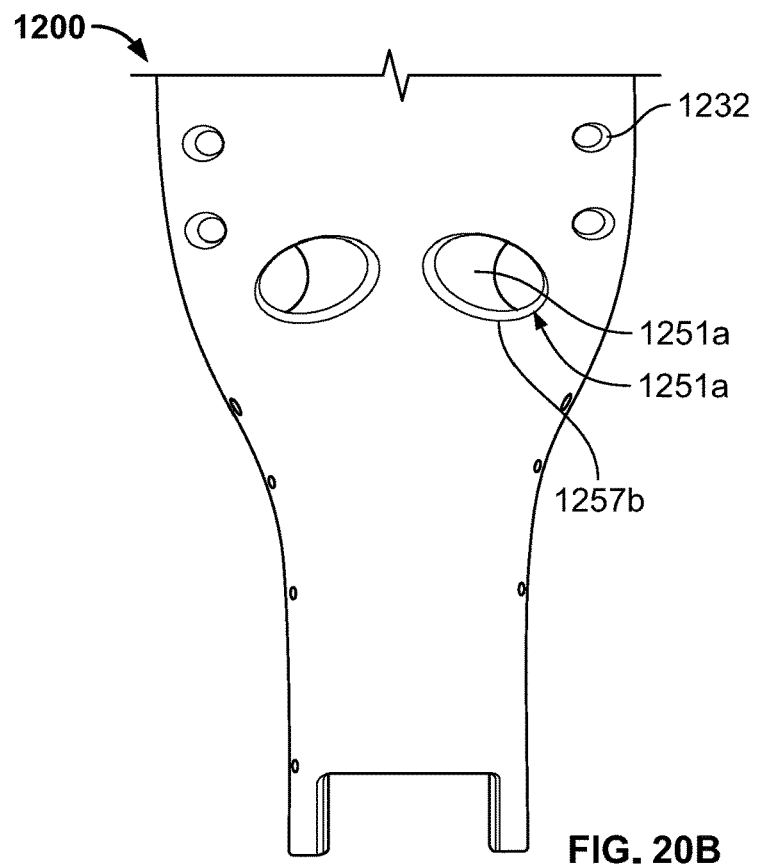
FIG. 20B is a rear elevational view of the joint replacement prosthesis of FIG. 20A.

However, through-slots 1258 are differently configured than slots 1058. In this regard, slots 1258 each extend through posterior and anterior sides of prosthesis 1210 such that each slot 1258 defines an anterior or first aperture 1257a and posterior or second aperture 1257b. The posterior and anterior apertures 1257a-b, as best shown in FIGS. 20A and 20B, are both elliptical in shape such that their respective major axes (i.e., an ellipses major axis) extend in a generally mediolateral direction. In addition, each slot 1258 is defined along its anteroposterior traversal by first and second opposing sidewalls 1251a-b. First sidewall 1251a, which is closer to a midline longitudinal axis of prosthesis 1210, is convexly curved generally about such midline axis. Conversely, the second sidewall 1251b is concavely curved but also generally about the midline axis of prosthesis 1210. In addition, as best shown in FIG. 20E, opening 1258 has a narrower opening in a proximal-distal direction near the center of opening 1258 while being wider nearer the anterior and posterior apertures 1257a-b. In other words, opening 1258 gradually narrows from posterior aperture 1257b to a center of opening 1258 and then gradually widens from the center of opening 1258 to anterior aperture 1251a.

The depicted embodiment allows filamentary fixation device 640 (or also 1100, 1100', 1100") to be threaded through slots 1258 similar to that described above with respect to assembly 1000. However, the narrowing and widening of openings 1258 in addition to their elliptical shape causes a flat filamentary fixation device to slightly fold over itself as it extends from posterior aperture 1257b to anterior aperture 1257b and vice versa. This allows filamentary fixation device 640 to conform to convex inner surface 1251a while being manipulable at the anterior side of prosthesis 1210 so that free ends 640a-b of fixation device 640 can be oriented at any desired angle without awkward crimping or bunching thereof. In this regard, prosthesis 1210 allows fixation device 640 to achieve any of the orientations previously described and more such that an extensor mechanism can be connected thereto in the manner previously described.

Figure 20C:
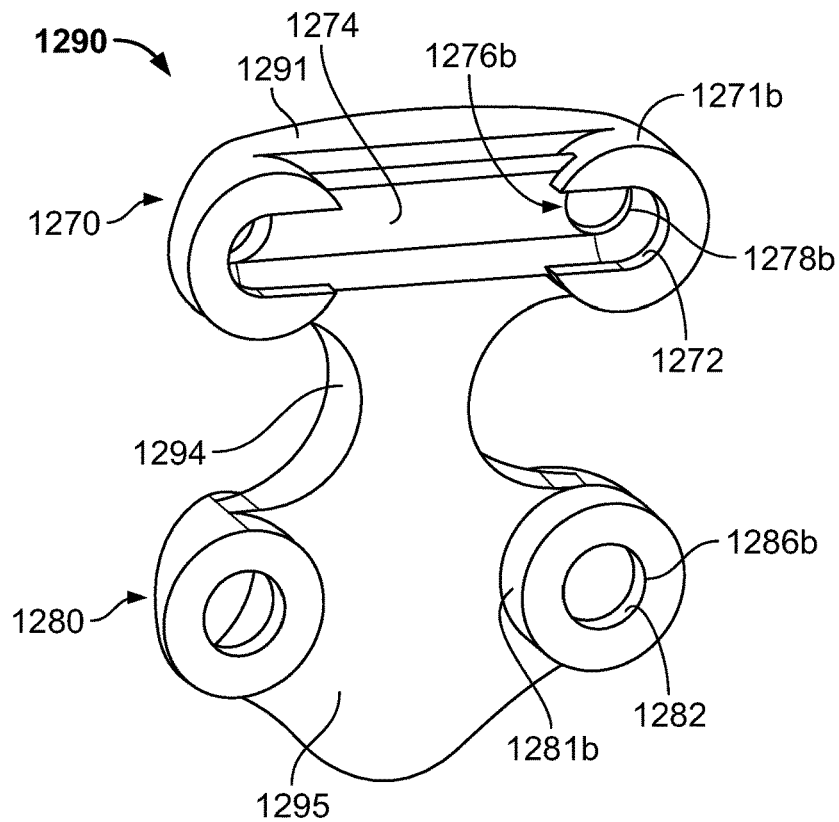
FIG. 20C is a rear perspective view of the connection plate of FIG. 20A.
Figure 20D:
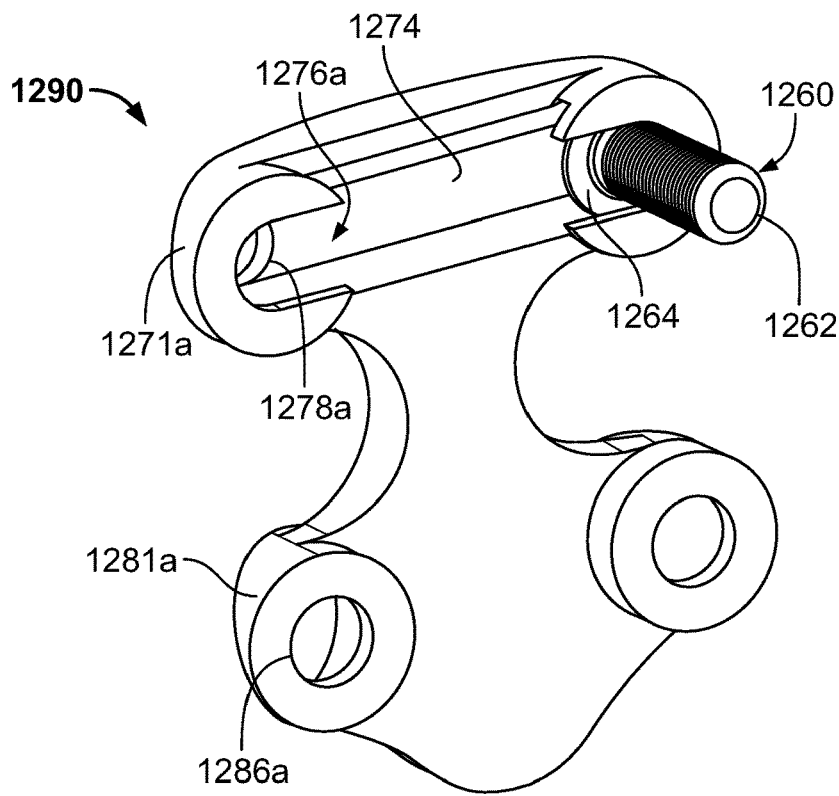
FIG. 20D is rear perspective view of the connection plate of FIG. 20A including a fastener assembled therewith.
Figure 20E:
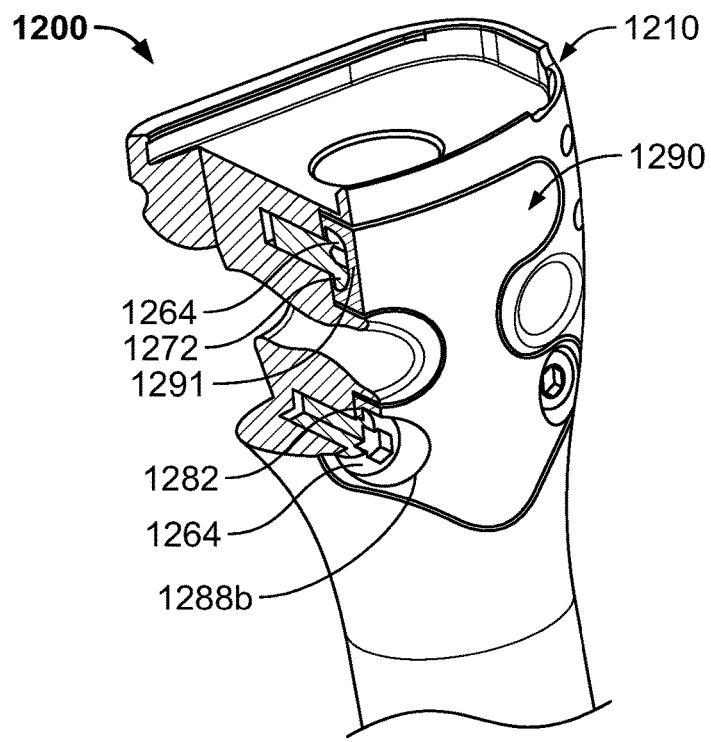
FIG. 20E is a cutaway perspective view of the joint replacement prosthesis of FIG. 20A.
Figure 20F:
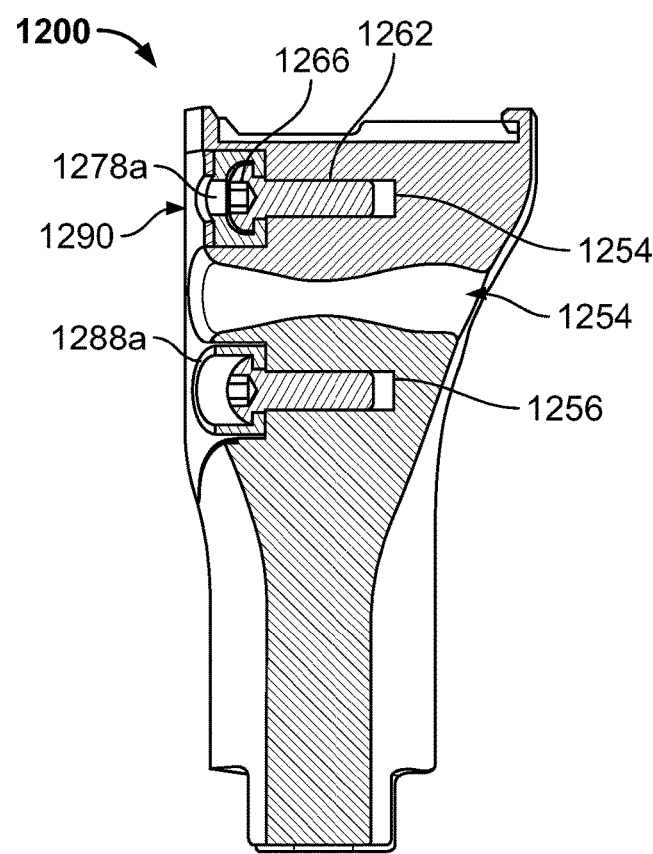
FIG. 20F is a side cross-sectional view taken along line F-F of FIG. 20A.

Connection plate or ingrowth plate 1290, as shown in FIGS. 20C and 20D, include a plate body 1291 that has a thickness extending between an anterior face 1292 and a posterior face 1295 thereof. Anterior face 1292 (see FIG. 20D) preferably includes a porous material extending over at least a portion of its area in order to promote tissue ingrowth therein. Plate 1290 includes a proximal portion 1270, a distal portion 1280, and an intermediate member 1294 extending therebetween. Distal portion 1280 includes a first and second boss 1281a-b extending posteriorly from the posterior face 1295. A first and second through-opening 1286a-b respectively extend through bosses 1281a-b from the anterior side to the posterior side of plate body 1291. Distal portion 1280 also includes a first and second counterbore 1288a-b each of which are respectively coaxial with first and second through-openings 1278a-b. Such configuration forms a circular rim 1282 between each counterbore and through-opening pairing. First and second openings 1286a-b are each configured to receive a threaded shaft 1262 of screw 1260. However, openings 1286a-b each have a cross-sectional dimension smaller than that of a head 1264 of screw 1260 such that head 1264 is prevented from passing therethrough, but is capable of being disposed within each of counterbores 1288a-b as best shown in FIGS. 20E and 20F. In this regard, screw 1260 is engaged to distal portion 1280 via the anterior side of plate body 1281 such that threaded shaft 1262 is passed through one of counterbores 1288a-b and then through respective through-opening 1286a-b so that head 1264 rests against rim 1282 from within counter bore 1288a or 1288b.

Proximal portion 1270 also includes a first and second boss 1271a-b extending posteriorly from posterior face 1295. However, proximal portion 1270 does not include counterbores. In addition, bosses 1271a-b each include a respective side-slot 1276a-b that defines a U-shaped rim 1272. A groove 1274 extends along posterior face 1295 in a mediolateral direction and communicates with side-slots 1276a-b. A first and second through-opening 1278a-b extend through the anterior face 1292 and posterior face 1295 and each intersect a respective side-slot 1276a-b. First and second through-openings 1278a-b each have a cross-sectional dimension smaller than that of screw head 1264. Unlike distal portion, a screw 1260 is engaged to proximal portion 1270 via the posterior side of plate body 1291 such that head 1264 is inserted into groove 1274 and slide along posterior surface 1295 and into one of side slots 1276a-b. Once disposed within one of side-slots 1276a-b, head 1264 rests on rim 1272 and is positioned between rim 1272 and a respective through-opening 1278a-b. In this regard, through-opening 1278a or 1278b aligns with a tool opening within head 1264 of screw so that a tool/driver can engage screw 1260 which is rotatably positioned within one of side-slots 1276a-b despite being positioned on the posterior side of plate body 1291, as best shown in FIG. 20D. However, threaded shaft 1262 extends posteriorly from side-slot 1276a-b for engagement with one of threaded openings 1254 of prosthesis 1210. This configuration reduces the overall footprint of through-openings 1278a-b relative to anterior surface 1292 of plate body 1291 as compared to that of counterbores 1288a-b. As such, more surface area of plate body 1291 can be dedicated to a porous surface for ingrowth particularly in the proximal portion 1270 of plate 1290 which is more likely to be in direct contact with soft tissue than distal portion 1280.

However, it should be understood that proximal portion 1270 can be configured the same as distal portion 1280 such that proximal portion 1270 includes counterbores, such as counterbores 1288a-b, for screw loading via the anterior side of plate body 1291. Alternatively, distal portion 1280 may be configured the same as proximal portion 1270 such that distal portion 1280 includes side-slots, such as side-slots 1276a-b, so that screw 1260 can be loaded from the posterior side of plate 1290. Also, it should be understood that in some embodiments, plate 1290 may not include bosses 1271a-b or 1281a-b, and may instead just have extra plate thickness. Moreover, in some embodiments, plate 1290 may not include groove 1274. However, groove 1274 is helpful to make space for head 1264 of screw 1260.

Proximal portion 1270 and distal portion 1280 are connected via intermediate member 1294 such that plate body 1291 has an hour-glass shape. In other words, proximal portion 1270 and distal portion 1290 are wider than at intermediate portion 1294. This configuration creates indentations at the sides of plate body 1291 to make space for openings 1258 of FIGS. 20A and 20B. FIGS. 20E and 20F illustrate the connection between plate 1290 and prosthesis 1210. In this regard, plate 1290 is disposed in an anterior recess of prosthesis 1210 with conforms to the shape of plate body 1290. Porous anterior face 1292 is positioned outward at the anterior side of prosthesis 1210 so as to engage tissue when implanted, as described above with respect to other embodiments of the present disclosure. Screws 1260 pass through distal portion 1280 such that threaded shafts 1262 engage threaded openings 1256 and heads 1264 engage circular rim 1282 from within counterbores 1288a-b. Additional screws 1260 are positioned at posterior side of plate 1290 within side-slots 1276a-b such that threaded shafts 1262 extend from plate body 1291 and into threaded openings 1254. In this regard, each head 1264 is sandwiched between rim 1272 and at least a portion of the thickness of plate body 1291.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, although embodiments of the invention have generally been described in reference to an orthopedic assembly in a tibia, the principles described herein are equally applicable to bones of other joints.

The invention claimed is:

1. An orthopedic assembly, comprising:
a tibial prosthesis having an anterior side, a posterior side, and first and second openings each extending therethrough from the anterior side to the posterior side, the first and second openings respectively being defined at least in part by a first sidewall, the first sidewall of the first opening including an interior convex surface portion extending along a length direction of the first opening such that a first width of the first opening at the convex surface portion is narrower than a second width of the first opening at one of the anterior and posterior sides; and
a filamentary fixation device made from a filamentary material having a longitudinal axis, a width, and a thickness, the width and thickness extending perpendicular to the longitudinal axis, the width being greater than the thickness, and the width and length defining a first side and an opposed second side of the filamentary fixation device,
wherein the filamentary fixation device extends through the first and second openings such that the first side of the filamentary fixation device faces outwardly away from the tibial prosthesis and the second side of the filamentary fixation device faces inwardly toward the tibial prosthesis.

2. The assembly of claim 1, wherein the tibial prosthesis further includes a patch of porous material on the anterior side between the first and second openings.

3. The assembly of claim 1, wherein the filamentary material is a woven material configured to promote tissue ingrowth.

4. The assembly of claim 1, wherein the filamentary material includes first and second free ends and an intermediate portion disposed therebetween, the first and second free ends overlapping at the anterior side of the tibial prosthesis, the intermediate portion being positioned at the posterior side of the tibial prosthesis and extending between the first and second openings.

5. The assembly of claim 4, wherein the intermediate portion extends perpendicular to a vertical plane bisecting the body of the tibial prosthesis, and the first and second free ends are oriented by the respective first and second openings such that they each extend therefrom in a direction oblique to the vertical plane.

6. The assembly of claim 1, wherein the first and second openings each define an anterior aperture at the anterior side of the tibial prosthesis and a posterior aperture at the posterior side of the tibial prosthesis.

7. The assembly of claim 6, wherein the first opening further comprises a second sidewall opposing the first side wall, the first sidewall being closer to a longitudinal axis of the tibial prosthesis than the second sidewall.

8. The assembly of claim 7, wherein the second sidewall includes a second convex surface portion such that apices of the first and second convex surface portions define a neck of the first opening.

9. The assembly of claim 7, wherein the anterior and posterior apertures of each opening are elliptical in shape.

10. The assembly of claim 6, wherein the anterior aperture is triangular, and the posterior aperture is pill shaped.

11. The assembly of claim 1, wherein the tibial prosthesis includes a metaphyseal portion and diaphyseal portion, the metaphyseal portion defining a tibial tray configured to receive a tibial insert for articulation with a femoral component, the diaphyseal portion being configured to connect to a diaphysis of a tibia, the first and second openings extending through the metaphyseal portion.

12. An orthopedic assembly, comprising:
a tibial prosthesis having an anterior side, a posterior side, and first and second openings extending therethrough from the anterior side to the posterior side, the first and second openings each defining an anterior aperture and a posterior aperture and each being defined by a first sidewall and a second sidewall; and
a filamentary fixation device having first and second free ends extending from the respective first and second openings and an intermediate portion extending between the first and second openings, the intermediate portion having a first orientation and the first and second free ends engaging the first sidewall so that they each have a second orientation different from the first orientation,
wherein the first opening tapers from the anterior aperture and from the posterior aperture such that an interior portion of the first opening has an interior width dimension less than a first exterior width dimension of the first opening at the anterior aperture or a second exterior width dimension of the first opening at the posterior aperture,
wherein the interior portion of the first opening includes a convex surface portion extending along a length direction of the first opening.

13. The assembly of claim 12, wherein the anterior aperture is elliptical.

14. The assembly of claim 12, wherein the second sidewall is parallel to a longitudinal axis of the tibial prosthesis.

15. The assembly of claim 14, wherein the second sidewall tilts away from the longitudinal axis of the tibial prosthesis along a traversal of the first sidewall from the posterior aperture to the anterior aperture.

16. The assembly of claim 12, wherein the filamentary fixation device is an elongate flat strip of filamentary material.

17. The assembly of claim 16, wherein the filamentary fixation device comprises a plurality of layers of mesh material.

18. The assembly of claim 12, wherein the first and second free ends of the filamentary fixation device overlap to form an X-shaped shaped arrangement.

19. The assembly of claim 18, wherein the tibial prosthesis includes a patch of porous material between the first and second openings.

* * * * *